US010631763B2

(12) United States Patent
Li et al.

(10) Patent No.: US 10,631,763 B2
(45) Date of Patent: *Apr. 28, 2020

(54) METHOD FOR GLUCOSE MONITORING

(71) Applicant: Taiwan Biophotonic Corporation, Hsinchu (TW)

(72) Inventors: Yu-Tang Li, Hsinchu (TW); Chang-Sheng Chu, Hsinchu (TW); Pei-Fang Tsou, Hsinchu (TW); Pei-Cheng Ho, Hsinchu (TW); Kuan-Jui Ho, Hsinchu (TW)

(73) Assignee: Taiwan Biophotonic Corporation, Hsinchu (TW)

( * ) Notice: Subject to any disclaimer, the term of this patent is extended or adjusted under 35 U.S.C. 154(b) by 278 days.

This patent is subject to a terminal disclaimer.

(21) Appl. No.: 15/650,969

(22) Filed: Jul. 16, 2017

(65) Prior Publication Data

US 2017/0311853 A1 Nov. 2, 2017

Related U.S. Application Data

(63) Continuation of application No. 13/457,517, filed on Apr. 27, 2012, now Pat. No. 9,743,864.

(Continued)

(51) Int. Cl.
*A61B 5/1455* (2006.01)
*A61B 5/145* (2006.01)

(52) U.S. Cl.
CPC ...... *A61B 5/14532* (2013.01); *A61B 5/14558* (2013.01)

(58) Field of Classification Search
CPC . A61B 5/0059; A61B 5/1455; A61B 5/14551; A61B 5/14552; A61B 5/14532; A61B 5/14558
See application file for complete search history.

(56) References Cited

U.S. PATENT DOCUMENTS 5,009,230 A * 4/1991 Hutchinson ........ A61B 5/14558
356/368
5,535,743 A * 7/1996 Backhaus .......... A61B 5/14558
600/310

(Continued)

FOREIGN PATENT DOCUMENTS

WO 01/22871 A1 4/2001

OTHER PUBLICATIONS

Michael F. G. Wood et al., "Combined optical intensity and polarization methodology for analyte concentration determination in simulated optically clear and turbid biological media", Journal of Biomedical Optics, Jul./Aug. 2008, pp. 044037-1 to 044037-9, vol. 13(4), International Society for Optical Engineering, US.

*Primary Examiner* — Eric F Winakur
*Assistant Examiner* — Chu Chuan Liu
(74) *Attorney, Agent, or Firm* — ScienBiziP, P.C.

(57) ABSTRACT

A method for non-invasive glucose monitoring includes the following steps. At least one ray of light is emitted from at least one light source. The light emitted from the light source is leaded into an eyeball and focused on the eyeball through a first beam splitter. The reflected light reflected from the eyeball is transmitted through the first beam splitter to a set of photo detectors. Optical angular information and energy information of the reflected light transmitted to the set of photo detectors are measured. Optical angular difference and energy difference resulting from the light emitted from the light source and the reflected light transmitted to the set of photo detectors are obtained. Glucose information is obtained by analyzing the optical angular difference and the energy difference. Since glucose information has a corresponding relationship with blood glucose information, blood glucose information may be obtained.

18 Claims, 29 Drawing Sheets

Related U.S. Application Data

(60) Provisional application No. 61/480,386, filed on Apr. 29, 2011, provisional application No. 61/508,078, filed on Jul. 15, 2011.

(56) References Cited

U.S. PATENT DOCUMENTS

| | | | |
|---|---|---|---|
| 6,152,875 A | 11/2000 | Hakamata | |
| 6,226,089 B1 * | 5/2001 | Hakamata | A61B 5/14532 356/432 |
| 2005/0154269 A1 | 7/2005 | Cameron | |
| 2010/0234704 A1 | 9/2010 | Cameron | |

* cited by examiner

METHOD FOR GLUCOSE MONITORING

CROSS-REFERENCE TO RELATED APPLICATIONS

This application is a continuation-in-part application of U.S. patent application Ser. No. 13/457,517 filed on Apr. 27, 2012, which is a non-provisional application of U.S. provisional application Ser. No. 61/480,386 filed on Apr. 29, 2011 and U.S. provisional application Ser. No. 61/508,078, filed on Jul. 15, 2011. The entire disclosures of the prior applications are considered to be part of the disclosure of the accompanying application and are hereby incorporated by reference.

FIELD

The disclosure generally relates to a method for non-invasive monitoring of glucose levels in blood supply of the body.

BACKGROUND

Diabetes is a clinical syndrome caused by factors such as absolute or relative lack of insulin in the body, abnormal secretion time, disorder, or resistance of insulin effector, etc. If the diabetes is not suitably controlled, it may cause some acute complications such as hypoglycemia, ketoacidosis, nonketotic hyperosmolar coma, etc. Also, it may cause some serious long-term complications such as cardiovascular diseases, chronic renal failure, retinopathy, neuropathy, microvascular diseases, etc.

Constantly blood glucose monitoring is essential for diabetics. A primary objective for treating diabetics is to maintain a normal concentration of blood glucose. Once a patient carefully controls his/her blood glucose, occurrence of the above-mentioned complications can be effectively prevented.

Presently, diabetics generally use blood glucose monitors to monitor the blood glucose. However, blood collection via fingertip pricking has to be performed prior to measuring the concentration of the blood glucose by a blood glucose monitor. The fingertip pricking is an invasive (destructive) sampling method for blood collection, which is relatively complicated and may cause pain, encouraging an unwillingness to periodically monitor the blood glucose.

Therefore, methods for non-invasive blood glucose monitoring become a development trend in blood glucose detection field. Most existing non-invasive glucose meters perform the blood glucose measurement by reference to skin blood glucose of human body through one single method (for example, an acoustic method, an optical method, or an electrical method). However, as skin is composed of epidermis, dermis, subcutaneous tissues, and different tissues, blood vessels and water in the skin may generate light scattering and/or light absorption, which may influence the measuring process and accordingly influence the accuracy of the measured concentration of blood glucose.

BRIEF DESCRIPTION OF THE DRAWINGS

Implementations of the present disclosure will now be described, by way of example only, with reference to the accompanying drawings.

DETAILED DESCRIPTION

Figure 1A:
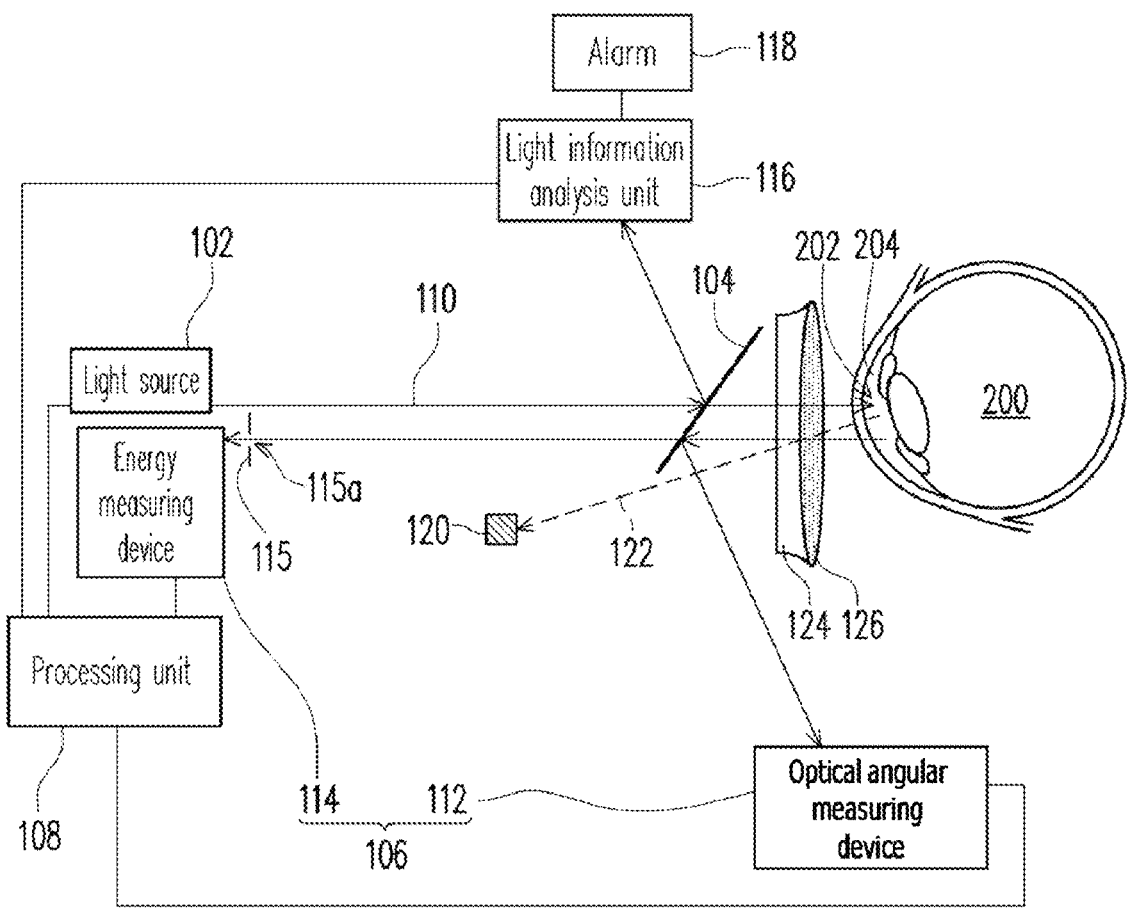
FIG. 1A is a schematic diagram illustrating an apparatus for non-invasive glucose monitoring in accordance with a first exemplary embodiment.

It will be appreciated that for simplicity and clarity of illustration, where appropriate, reference numerals have been repeated among the different figures to indicate corresponding or analogous elements. In addition, numerous specific details are set forth in order to provide a thorough understanding of the exemplary embodiments described herein. However, it will be understood by those of ordinary skill in the art that the exemplary embodiments described herein can be practiced without these specific details. In other instances, methods, procedures, and components have not been described in detail so as not to obscure the related relevant feature being described. Also, the description is not to be considered as limiting the scope of the exemplary embodiments described herein. The drawings are not necessarily to scale and the proportions of certain parts have been exaggerated to better illustrate details and features of the present disclosure.

Several definitions that apply throughout this disclosure will now be presented.

The term "substantially" is defined to be essentially conforming to the particular dimension, shape, or other feature that the term modifies, such that the component need not be exact. For example, substantially cylindrical means that the object resembles a cylinder, but can have one or more deviations from a true cylinder. The term "comprising," when utilized, means "including, but not necessarily limited to"; it specifically indicates open-ended inclusion or membership in the so-described combination, group, series and the like.

The disclosure provides an apparatus for non-invasive glucose monitoring capable of accurately measure a glucose information (e.g., concentration of glucose) of a measuring object, and since the glucose information (e.g., concentration of glucose) in an eyeball (e.g., aqueous humor within eyeball) has a corresponding relationship with a blood glucose information (e.g., concentration of blood glucose), the blood glucose information (e.g., concentration of blood glucose) may be read.

The disclosure also provides a method for non-invasive blood glucose monitoring to measure concentration of glucose in real time.

Figure 1B:
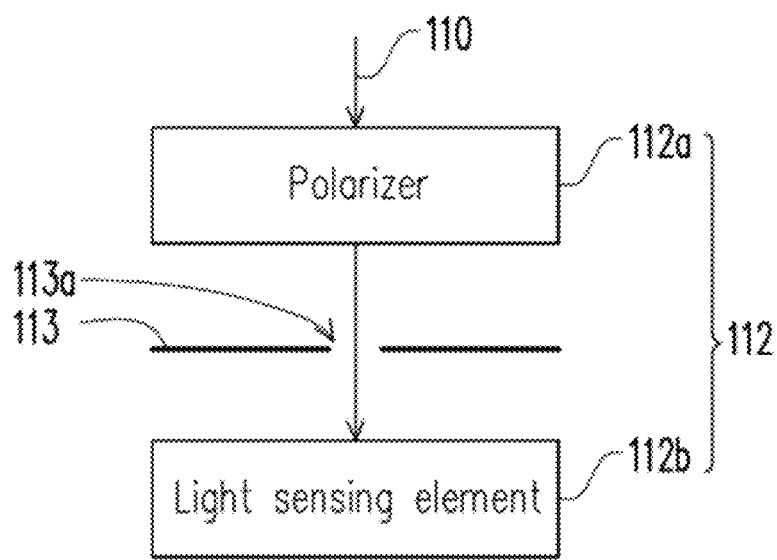
FIG. 1B is a schematic diagram illustrating an optical angular measuring device in FIG. 1A.

FIG. 1A is a schematic diagram illustrating an apparatus for non-invasive glucose monitoring in accordance with a first exemplary embodiment. FIG. 1B is a schematic diagram illustrating an optical angular measuring device from FIG. 1A in accordance with the first exemplary embodiment.

With reference to FIG. 1A, an apparatus for non-invasive glucose monitoring 100 which comprises a light source 102, a first beam splitter 104, a set of photo detectors 106, and a processing unit 108. The apparatus for non-invasive blood glucose monitoring 100 may, for example, detect concentration of glucose of an aqueous humor 204 in an anterior chamber 202 of an eyeball 200.

The light source 102 generates at least one ray of light 110. The light source 102 is, for example, a light emitting diode (LED), a laser diode, or other light source. A wavelength of the light source 102 is, for example, which can be absorbed by glucose molecules and namely, a wavelength that is capable of being absorbed by the glucose molecules in the eyeball 200, such as an infrared light. The light 110 emitted from the light source 102 comprises a linear polarized light, a circular polarized light, an elliptical polarized light, or a partial polarized light. Moreover, the light source 102 may have a function for controlling an emitting frequency of the light 110, which avails the photo detector set 106 in determining the light to be measured according to the emitting frequency. In addition, the light source 102 may have a function for controlling an intensity of the light 110, which assures the light entering into the eyeball 200 is unable to cause any harm. Furthermore, the light source 102 may have a function for controlling a length of turn-on time of the light 110 and controlling a length of turn-off time of the light 110, or a combination thereof, which provides a glucose detection time on one hand but also ensures that the light energy entering into the eyeball 200 is unable to cause any harm on the other hand. Although, in the present exemplary embodiment, the single light 110 emitted from the single light source 102 is taken as an example for description, the disclosure is not limited thereto; and, in another exemplary embodiment, types of the light source 102 and types of the light 110 may be two or more.

The first beam splitter 104 with a focusing function which can lead the light 110 emitted from the light source 102 into an eyeball 200 and focus on the eyeball 200 through the first beam splitter 104. The first beam splitter 104 is, for example, focusing the light 110 into the anterior chamber 202 of the eyeball 200, and the reflected light 111 reflected from the eyeball 200 comprises the reflected light reflected from the aqueous humor 204. The first beam splitter 104 is, for example, an optical film, a lens, a grating, a diffractive optic device or a combination of any the above elements.

The set of photo detectors 106 measures an optical angular information and an absorption energy information of the reflected light 111 reflected from the eyeball 200 and then transmitted through the first beam splitter 104 to the set of photo detectors 106. In the present exemplary embodiment, the set of photo detectors 106 comprises an optical angular measuring device 112 and an energy measuring device 114. Wherein, the optical angular measuring device 112 is used for measuring the optical angular information of the reflected light 111 reflected from the eyeball 200 and then transmitted through the first beam splitter 104, and the energy measuring device 114 is used for measuring the absorption energy information of the reflected light 111 reflected from the eyeball 200 and then passed through the first beam splitter 104.

In another exemplary embodiment, the optical angular measuring device 112 and the energy measuring device 114 may be exchanged. Namely, the optical angular measuring device 112 is used to measure the optical angular information of the reflected light 111 reflected from the eyeball 200 and then passed through the first beam splitter 104, and the energy measuring device 114 is used to measure the absorption energy information of the reflected light 111 reflected from the eyeball 200 and then reflected by the first beam splitter 104.

With reference to FIG. 1B, the optical angular measuring device 112 comprises a polarizer 112a and a light sensing element 112b, wherein the light is firstly passed through the polarizer 112a, and then transmitted to the light sensing element 112b. The optical angular measuring device 112 is, for example, an active optical angular measuring device or a passive optical angular measuring device, wherein a measurement angle of the active optical angular measuring device may be changed whereas a measurement angle of the passive optical angular measuring device is fixed. The active optical angular measuring device is, for example, an analyzer which may directly calculate the optical angular information. The passive optical angular measuring device measures the energy of the reflected light 111 that passed through a polarizer 112a using the light sensing element 112b to calculate the optical angular information of the optical angular information. The energy measuring device 114 is, for example, a light sensing element such as a charge coupled device (CCD), a complementary metal oxide semiconductor sensors or a light emitting diode.

Moreover, with reference to FIGS. 1A and 1B, the apparatus for non-invasive glucose monitoring 100 may further selectively comprise at least one of a light barrier 113 and a light barrier 115. The light barrier 113 has an opening 113a, and the opening 113a, through assembly, may enable the reflected light 111 to pass through the light barrier 113, and then transmit to the light sensing element 112b. The light barrier 113 is, for example, disposed between the polarizer 112a and the light sensing element 112b, but the disclosure is not limited thereto. In other exemplary embodiments, the light barrier 113 may further enable the reflected light 111 to pass through the polarizer 112a and then through the opening 113a of the light barrier 113. In addition, the light barrier 115 has an opening 115a, and the opening 115a, through assembly, may enable the reflected light 111 to pass through the light barrier 115, and then transmit to the energy measuring device (e.g., light sensing element). The light barriers 113, 115 respectively are, for example, a metal photomask or a silica glass photomask. The light barriers 113, 115 respectively may prevent stray light from entering into the optical angular measuring device 112 and the energy measuring device 114, and thus may reduce interference from the stray light, so as to enhance the signal to noise ratio (S/N ratio). It is noted that each of the following exemplary embodiments, through the light barrier, may reduce the influence of stray light on the measurement results of the optical angular measuring device and of the energy measuring device; however, further elaboration on the light barrier in the other exemplary embodiments are omitted in order to simplify the description.

Referring to FIG. 1A again, the processing unit 108 is, for example, coupled to the optical angular measuring device 112 and the energy measuring device 114 of the set of photo detectors 106, and receives and processes the optical angular information and the absorption energy information to obtain an optical angular difference and an absorption energy difference between the light 110 emitted from the light source 102 and the reflected light 111 transmitted to the set of photo detectors 106, and to obtain biological molecule information, which at least comprises a glucose, by analyzing the optical angular difference and the absorption energy difference. The processing unit obtains the glucose information through analyzing the biological molecule information. The biological molecule is, for example, cholesterol, uric acid, water, lactic acid, urea, ascorbic acid, or a combination thereof. Moreover, the biological molecule may comprise one kind of interference molecules therein, and the kind of interference molecule is, for example, one kind of molecule different from the measurement target (e.g., glucose), such as cholesterol, uric acid, water, lactic acid, urea, or ascorbic acid. As ascorbic acid and lactic acid may generate interference onto the optical angular information, whereas water may generate interference to the absorption energy information. During the process of obtaining the glucose information through the processing unit 108, the processing unit 108 may remove interference signals caused by the interference molecules. The processing unit 108 may also control a light quality, an opto-element offset or a combination thereof, and statistically analyze the optical angular information and the absorption energy information, so as to obtain the glucose information. The spatial variation of the light source comprises a light emitting frequency variation, a light energy intensity variation, a length variation of turn-on time of the light, a length variation of turn-off time of the light, or a combination thereof. Since the glucose concentration in the eyeball 200 (e.g., aqueous humor within eyeball) has a corresponding relationship with a blood glucose concentration, the blood glucose information (e.g., concentration of blood glucose) can be determined according to the corresponding relationship. The processing unit 108 is, for example, an analog digital circuit integration module, wherein the analog digital circuit integration module comprises a microprocessor, an amplifier and an analog digital converter (ADC). The analog digital circuit integration module may further comprise a wireless transmission device.

In the present exemplary embodiment, the processing unit 108 is, for example, coupled to the light source 102 to control an optical characteristic of the light 110 emitted from the light source 102.

The apparatus for non-invasive blood glucose monitoring 100 may selectively comprise a light information analysis unit 116 for detecting a light information of the light 110 from the first beam splitter 104 before the light 110 is transmitted into the eyeball 200, and selectively transmit the light information of the light 110 to the processing unit 108 or an alarm 118 to perform a feedback control with the optical characteristic of the light 110. The light information analysis unit 116 comprises at least one of an optical power meter and an optical sensor, the light information detected by the optical power meter is energy information whereas the light information detected by the optical sensor is at least one of energy information or position information. The optical characteristic of the light 110 is, for example, energy emittance and/or light position.

When the emitting energy of the light 110 emitted from the light source 102 is excessively high, the light 110 may cause harm to the eyeball 200. Therefore, when the processing unit 108 receives the energy information indicating excessive emitting energy of the light 110, the processing unit 108 will reduce the emitting energy of the light 110 emitted from the light source 102. On the other hand, when the alarm 118 receives the energy information indicating excessive emitting energy of the light 110, the alarm 118 sends a light or a sound warning signal to notify the user that the emitting energy of the light 110 emitted from the light source 102 is excessively high, and the emitting energy of the light 110 should be adjusted. Therefore, usage of the light information analysis unit 116 may prevent harming the eyeball 200 due to excessive emitting energy of the light 110.

Moreover, when the light position of the light 110 emitted from light source 102 is shifted, the accuracy of a blood glucose measurement is lowered. Therefore, when the processing unit 108 receives the position information indicating the light position of the light 110 is shifted, the processing unit 108 adjusts the light position of the light 110 emitted from the light source 102. On the other hand, when the alarm 118 receives the position information indicating the light position of the light 110 is shifted, the alarm 118 sends the light or the sound warning signal to notify the user that the light position of the light 110 emitted from the light source 102 is shifted, and the light position of the light 110 should be adjusted. Therefore, usage of the light information analysis unit 116 may prevent the light position of the light 110 from shifting, thus enhancing the accuracy of the blood glucose measurement.

In the present exemplary embodiment, the energy information detected by the light information analysis unit 116 is simultaneously transmitted to the processing unit 108 and the alarm 118; nevertheless, the feedback control may be implemented as long as the energy information is transmitted to one of the processing unit 108 and the alarm 118. The light information analysis unit 116 is, for example, respectively coupled to the processing unit 108 and the alarm 118, but a coupling manner of the light information analysis unit 116, the processing unit 108 and the alarm 118 is not limited thereto.

In another exemplary embodiment, the light source 102 is, for example, coupled to a light source control unit (not shown), and now the light information analysis unit 116 transmits the energy information of the light 110 to the light source control unit, so as to perform the feedback control for the light source 102.

In addition, before the light 110 is transmitted into the eyeball 200, the detection of the light 110 reflected by the first beam splitter 104 using the light information analysis unit 116 is taken as an example to describe the present exemplary embodiment.

Furthermore, the apparatus for non-invasive glucose monitoring 100 may further selectively comprise an eye-alignment position device 120 for aligning the sight-line of an eye 122 with the eye-alignment position device 120, so as to determine a measuring position of the eyeball 200. The eye-alignment position device 120 is, for example, a light spot, a marker, or a relief pattern.

On the other hand, the apparatus for non-invasive glucose monitoring 100 may further selectively comprise a joint element 124. A light outlet of the joint element 124, located at the apparatus for non-invasive glucose monitoring, is used for resting on an outer corner an eye. Moreover, the apparatus for non-invasive glucose monitoring 100 may further selectively comprise a protective cover 126 disposed on a surface of the joint element 124 that is used for resting on the outer corner of eye. The protective cover 126 is, for example, a disposable protective cover.

According to the first exemplary embodiment, the apparatus for non-invasive blood glucose monitoring 100 may simultaneously analyze the optical angular difference and the absorption energy difference between the light 110 emitted from the light source 102 and the reflected light 111 transmitted to the set of photo detectors 106, thus obtaining the glucose information (e.g., concentration of glucose), and since the glucose concentration in the eyeball 200 (e.g., aqueous humor within eyeball) has a corresponding relationship with a blood glucose concentration, the blood glucose information (e.g., concentration of blood glucose) with high accuracy is read through the corresponding relationship.

Moreover, the apparatus for non-invasive blood glucose monitoring 100 may be miniaturized in applications, for example, used in form of a headband or used in collaboration with glasses, so as to improve utilization convenience. In addition, the utilization environment of the apparatus for non-invasive blood glucose monitoring 100 has no special restriction, and thus may be utilized indoors or outdoors.

Figure 2:
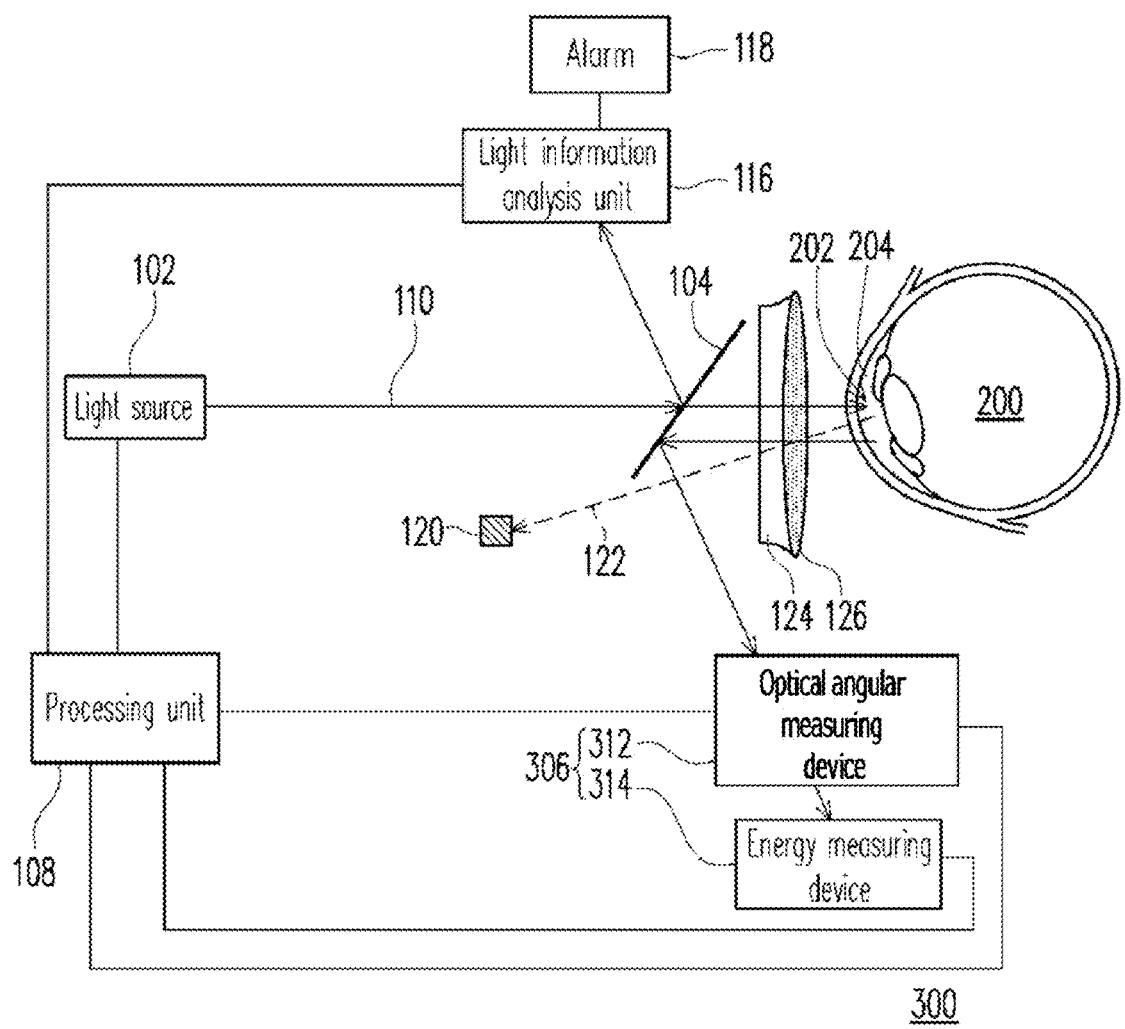
FIG. 2 is a schematic diagram illustrating an apparatus for non-invasive glucose monitoring in accordance with a second exemplary embodiment.

FIG. 2 is a schematic diagram illustrating an apparatus for non-invasive glucose monitoring in accordance with a second exemplary embodiment.

Referring to FIG. 1A and FIG. 2, a difference between the apparatus for non-invasive blood glucose monitoring 300 of the second exemplary embodiment and the apparatus for non-invasive blood glucose monitoring 100 of the first exemplary embodiment is that an optical angular measuring device 312 and an energy measuring device 314 in a set of photo detectors 306 of the second exemplary embodiment are located at a same side of the first beam splitter 104, and the optical angular measuring device 112 and the energy measuring device 114 in the set of photo detectors 106 of the first exemplary embodiment are located at two sides of the first beam splitter 104, respectively. The optical angular measuring device 312 and the energy measuring device 314 are, for example, coupled to the processing unit 108, respectively, but the disclosure is not limited thereto. Compositions, coupling relations and functions of the other components of the apparatus for non-invasive blood glucose monitoring 300 of the second exemplary embodiment are similar to that of the apparatus for non-invasive blood glucose monitoring 100 of the first exemplary embodiment, so that detailed descriptions thereof are not repeated.

In the present exemplary embodiment, the set of photo detectors 306 is, for example, used to measure the reflected light 111 reflected from the eyeball 200 and then reflected by the first beam splitter 104. The reflected light 111 to be measured is first transmitted to the optical angular measuring device 312 for measuring the optical angular information, and then transmitted to the energy measuring device 314 for measuring the absorption energy information. In another exemplary embodiment, the set of photo detectors 306 may also be used to measure the reflected light 111 reflected from the eyeball 200 and then passed through the first beam splitter 104.

In another exemplary embodiment, the apparatus for non-invasive blood glucose monitoring 300 further comprises another set of the optical angular measuring device 312 and the energy measuring device 314, so that the apparatus for non-invasive blood glucose monitoring 300 has two sets of the optical angular measuring device 312 and the energy measuring device 314 for respectively measuring the optical angular information and the absorption energy information of the reflected light 111 reflected from the eyeball 200 and then passed through the first beam splitter 104, and for measuring the optical angular information and the absorption energy information of the reflected light 111 reflected from the eyeball 200 and then reflected by the first beam splitter 104.

Similarly, the apparatus for non-invasive blood glucose monitoring 300 of the second exemplary embodiment may simultaneously analyze the optical angular difference and the absorption energy difference between the light 110 emitted from the light source 102 and the reflected light 111 transmitted to the set of photo detectors 306 to obtain the glucose information (e.g., concentration of glucose), and since the concentration of glucose in the eyeball 200 (e.g., aqueous humor within eyeball) has a relationship with a blood glucose concentration, the blood glucose information (e.g., concentration of blood glucose) with a high accuracy is read through the corresponding relationship. Moreover, the apparatus for non-invasive blood glucose monitoring 300 may be miniaturized, so that it is convenient in utilization, and may be utilized indoors or outdoors.

Figure 3:
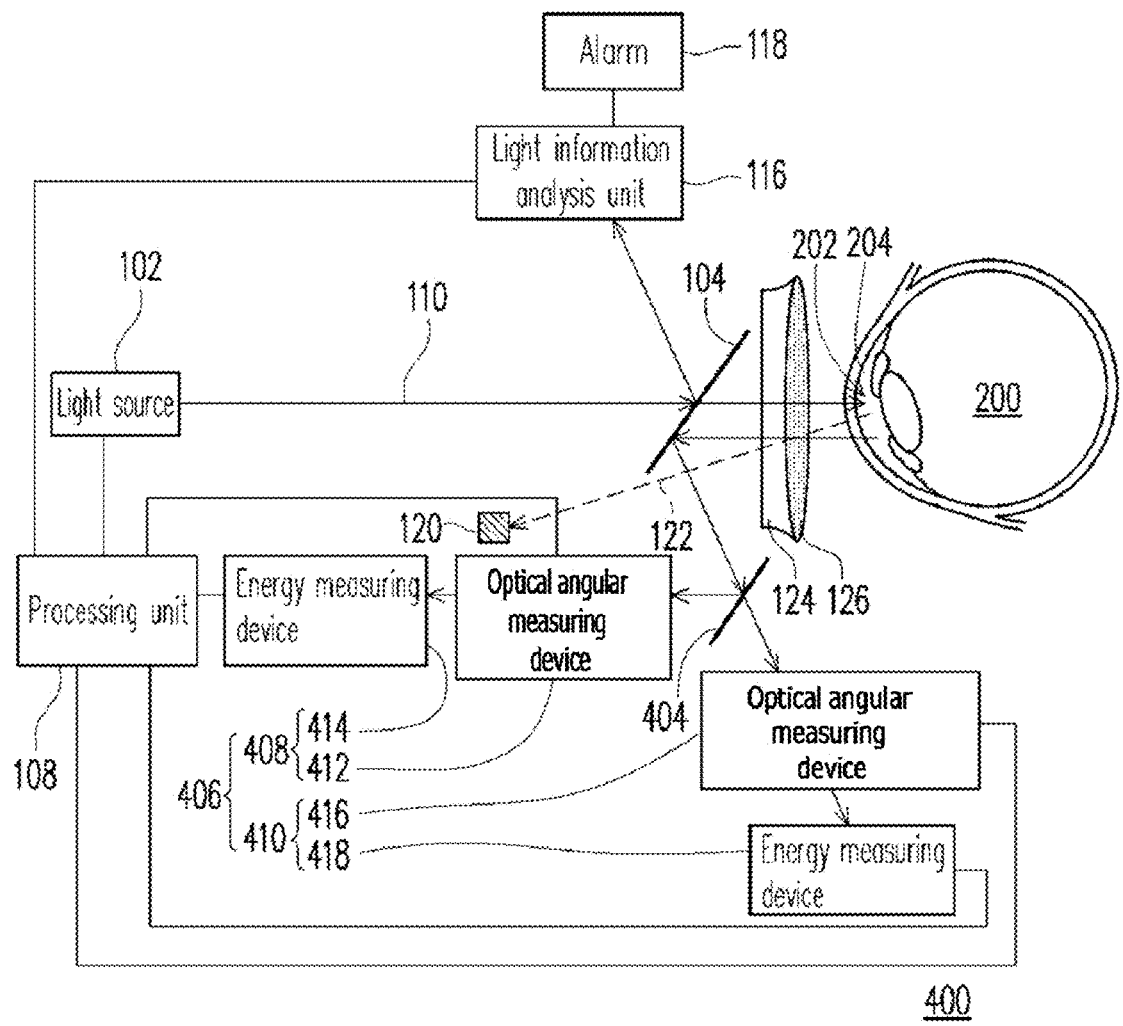
FIG. 3 is a schematic diagram illustrating an apparatus for non-invasive glucose monitoring in accordance with a third exemplary embodiment.

FIG. 3 is a schematic diagram illustrating an apparatus for non-invasive glucose monitoring in accordance with a third exemplary embodiment.

Referring to FIG. 1A and FIG. 3, a difference between an apparatus for non-invasive blood glucose monitoring 400 of the third exemplary embodiment and the apparatus for non-invasive blood glucose monitoring 100 of the first exemplary embodiment is that the apparatus for non-invasive blood glucose monitoring 400 of the third exemplary embodiment further comprises a second beam splitter 404, and a set of photo detectors 406 comprises a first photo detector 408 and a second photo detector 410. Compositions, coupling relations and functions of the other components of the apparatus for non-invasive blood glucose monitoring 400 of the third exemplary embodiment are similar to that of the apparatus for non-invasive blood glucose monitoring 100 of the first exemplary embodiment, so that detailed descriptions thereof are not repeated.

The second beam splitter 404 transmits the reflected light 111 reflected from the eyeball 200 and then transmitted through the first beam splitter 104 to the set of photo detectors 406. The second beam splitter 404 is, for example, an optical film, an optical lens, an optical grating, a diffractive optical element or a combination of any the above elements.

The first photo detector 408 is used to measure the reflected light 111 reflected by the second beam splitter 404, and the second photo detector 410 is used to measure the reflected light 111 passed through the second beam splitter 404. The first photo detector 408 comprises an optical angular measuring device 412 and an energy measuring device 414, and the second photo detector 410 comprises an optical angular measuring device 416 and an energy measuring device 418. The reflected light 111 to be measured is, for example, first transmitted to the optical angular measuring device 412 (or 416) for measuring the optical angular information, and then transmitted to the energy measuring device 414 (418) for measuring the absorption energy. Composition of the optical angular measuring device 412 (or 416) is similar to that of the optical angular measuring device 112, and composition of the energy measuring device 414 (or 418) is similar to the energy measuring device 114, so that descriptions thereof are not repeated. When the first photo detector 408 and the second photo detector 410 in the apparatus for non-invasive blood glucose monitoring 400 may simultaneously measure the optical angular information and the absorption energy, by cross-comparing the obtained two sets of the optical angular information and the absorption energy, the optical angular difference and the absorption energy difference between the light 110 emitted from the light source 102 and the reflected light 111 transmitted to the set of photo detectors 406 may be analyzed to obtain the glucose information (e.g., concentration of glucose), and since the glucose concentration in the eyeball 200 (e.g., aqueous humor within eyeball) has a relationship with the concentration of blood glucose, the blood glucose information (e.g., concentration of blood glucose) with high accuracy is read through the corresponding relationship. The optical angular measuring devices 412, 416 and the energy measuring devices 414, 418 are, for example, respectively coupled to the processing unit 108, but the disclosure is not limited thereto.

It is noted that when the optical angular measuring devices 412, 416 are all passive optical angular measuring devices and respectively comprise a polarizer, the polarizers in the optical angular measuring devices 412, 416 are, for example, one of a horizontal polarizer and a vertical polarizer, or two sets of polarizers with known optical angles. If the two sets of the polarizers with known optical angles are used, one of the measuring methods thereof compares energy differences of the two sets of the polarizers, and according to the energy differences, the optical angular difference within a certain range of glucose concentration is calculated, to improve the detection accuracy. Another method uses the two sets of polarizers with known optical angles to determine offset components according to the absorption energy differences, to calculate the optical angular information.

In another exemplary embodiment, one of the first photo detector 408 and the second photo detector 410 is, for example, a single optical angular measuring device, and another one of the first photo detector 408 and the second photo detector 410 is, for example, a single energy measuring device.

Although, in the aforementioned exemplary embodiment, the reflected light 111 reflected by the second beam splitter 404 and/or the reflected light 111 passed through the second beam splitter 404 is one ray of light. However, the reflected light 111 reflected by the second beam splitter 404 and/or the reflected light 111 passed through the second beam splitter 404 may be divided into two or more rays of light by the second beam splitter 404, and then measured by the aforementioned first photo detector 408 and the second photo detector 410.

According to the third exemplary embodiment, the apparatus for non-invasive blood glucose monitoring 400 may simultaneously analyze the optical angular difference and the absorption energy difference between the light 110 emitted from the light source 102 and the reflected light 111 transmitted to the set of photo detectors 406 to obtain the glucose information (e.g., concentration of glucose), and since the concentration of glucose in the eyeball 200 (e.g., aqueous humor within eyeball) has a relationship with the concentration of blood glucose, the blood glucose information (e.g., concentration of blood glucose) with a high accuracy is read through the corresponding relationship. Moreover, the apparatus for non-invasive blood glucose monitoring 400 may be miniaturized, so that it is convenient in utilization, and thus may be utilized indoors or outdoors.

Figure 4:
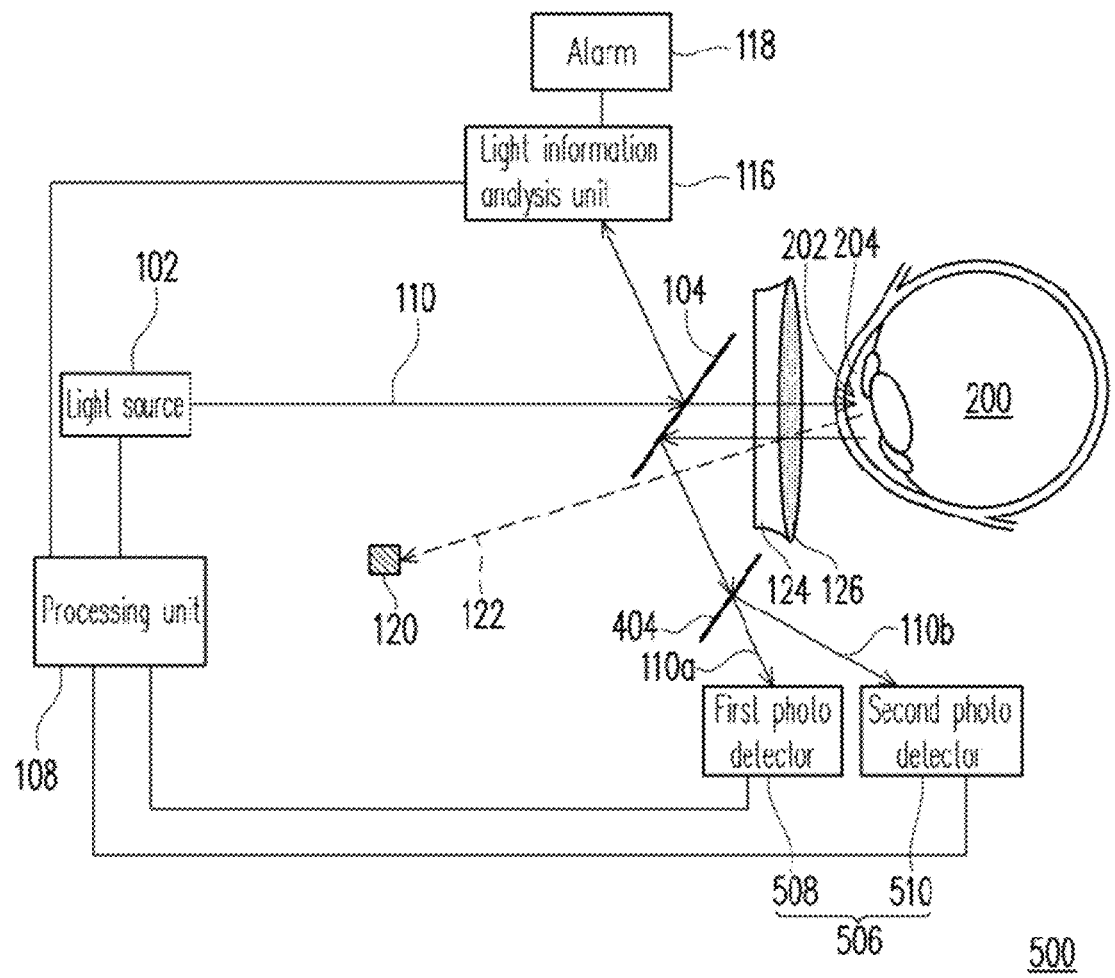
FIG. 4 is a schematic diagram illustrating an apparatus for non-invasive glucose monitoring in accordance with a fourth exemplary embodiment.

FIG. 4 is a schematic diagram illustrating an apparatus for non-invasive glucose monitoring in accordance with a fourth exemplary embodiment.

Referring to FIG. 3 and FIG. 4, a difference between an apparatus for non-invasive blood glucose monitoring 500 of the fourth exemplary embodiment and the apparatus for non-invasive blood glucose monitoring 400 of the third exemplary embodiment is that, in the apparatus for non-invasive blood glucose monitoring 500 of the fourth exemplary embodiment, a set of photo detectors 506 comprises a first photo detector 508 and a second photo detector 510, and the first photo detector 508 and the second photo detector 510 are located at a same side of the second beam splitter 404. In the present exemplary embodiment, the first photo detector 508 and the second photo detector 510 are, for example, located at the side of the second beam splitter 404 where the reflected light 111 passes there through, and are respectively used to measure two rays of reflected light 111a, 111b generated by the reflected light 111 after passed through the second beam splitter 404. One of the first photo detector 508 and the second photo detector 510 is, for example, an optical angular measuring device for measuring the optical angular information, and another one of the first photo detector 508 and the second photo detector 510 is, for example, an energy measuring device for measuring the absorption energy information. The first photo detector 508 and the second photo detector 510 are, for example, coupled to the processing unit 108, respectively, but the disclosure is not limited thereto. Compositions, coupling relations and functions of the other components of the apparatus for non-invasive blood glucose monitoring 500 of the fourth exemplary embodiment are similar to that of the apparatus for non-invasive blood glucose monitoring 400 of the third exemplary embodiment, so that detailed descriptions thereof are not repeated.

In another exemplary embodiment, the first photo detector 508 and the second photo detector 510 may also be located at the side of the second beam splitter 404, respectively, where the reflected light 111 is reflected, and are used to measure two rays of light generated by reflecting the reflected light 111 through the second beam splitter 404.

Although, in the aforementioned exemplary embodiment, the light 110 reflected by the second beam splitter 404 and/or the light 110 passed through the second beam splitter 404 are the reflected light 111a, 100b, the reflected light 111 reflected by the second beam splitter 404 and/or the reflected light 111 passed through the second beam splitter 404 may be divided into three or more rays of light by the second beam splitter 404 and then measured by the aforementioned first photo detector 508 and the second photo detector 510.

Similarly, the apparatus for non-invasive blood glucose monitoring 500 of the fourth exemplary embodiment may simultaneously analyze the optical angular difference and the absorption energy difference between the light 110 emitted from the light source 102 and the reflected light 111a,100b transmitted to the photo detector set 506 to obtain the glucose information (e.g., concentration of glucose), and since the concentration of glucose in the eyeball 200 (e.g., aqueous humor within eyeball) has a relationship with the corresponding concentration of blood glucose, the blood glucose information (e.g., concentration of blood glucose) with a high accuracy is read through the corresponding relationship. Moreover, the apparatus for non-invasive blood glucose monitoring 500 may be miniaturized, so that it is convenient in utilization, and thus may be utilized indoors or outdoors.

Figure 5:
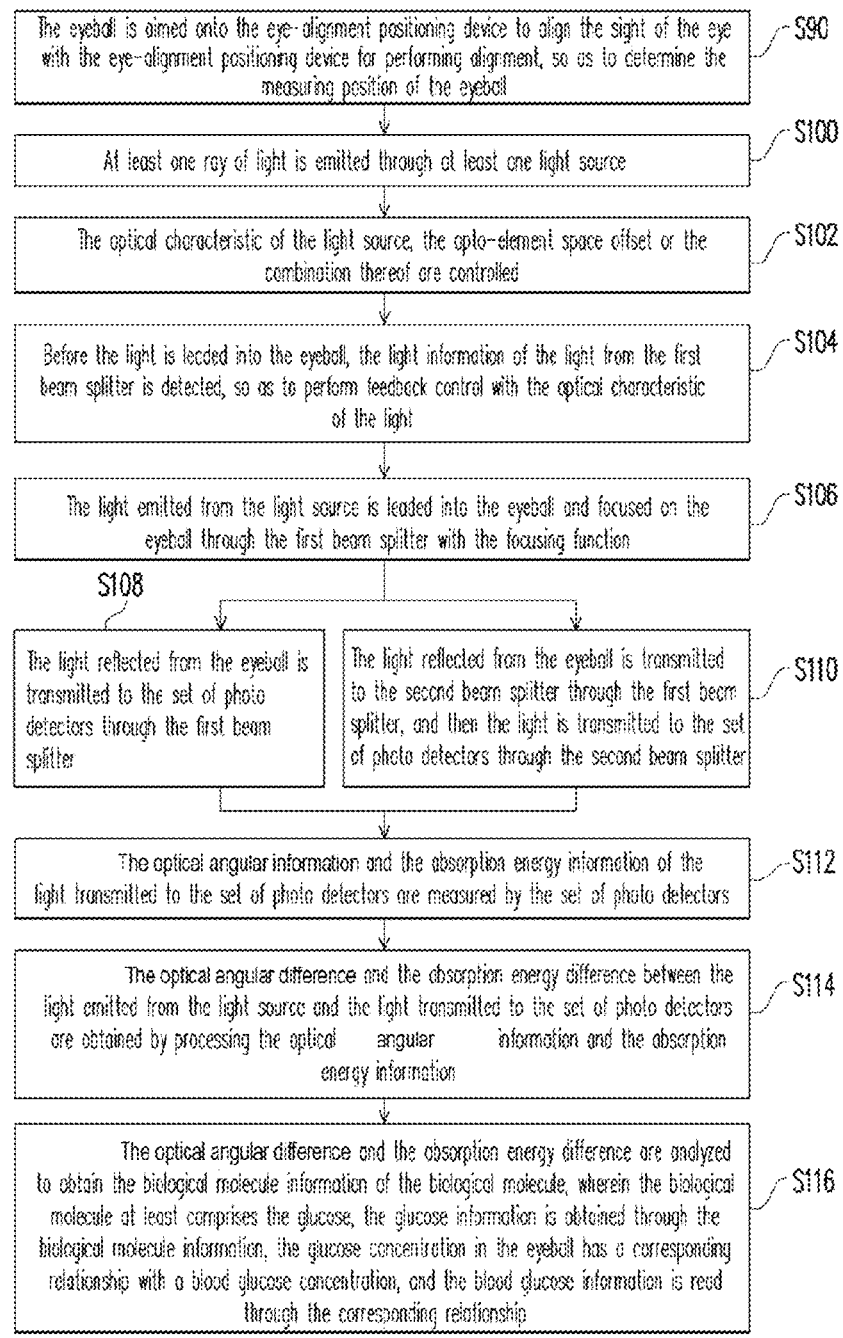
FIG. 5 is a flow chart diagram illustrating a method for a non-invasive blood glucose monitoring in accordance with a fifth exemplary embodiment.

FIG. 5 is a flow chart diagram illustrating a method for a non-invasive blood glucose monitoring in accordance with a fifth exemplary embodiment.

With reference to FIG. 5, firstly, step S90 may be selected and performed for aiming the eyeball onto the eye-alignment position device to align the sight-line of the eye with the eye-alignment position device for performing alignment, wherein the alignment includes adjusting a relative angle and a position between the optical axis of the eye-alignment position device and the sight-line of the eye, to determine a measuring position of the eyeball. Next, in step S100, at least one ray of light is emitted through at least one light source. Then, step S102 may be selectively performed for controlling the optical characteristic of the light source, the opto-element offset or the combination thereof, and a change factor is produced thus facilitates in analyzing the blood glucose information more accurately. Wherein, the light source is used to control an emitting frequency of the light, an intensity of the light, a length of turn-on time of the light, a length of turn-off time of the light, or a combination thereof. The set of photo detectors may assure the light to be measured according to the emitting frequency of the light. Moreover, by controlling the intensity of the light through the light source, it is ensured that the light energy entering the eyeball is unable to cause any harm. In addition, by controlling the length of turn-on time of the light, the length of turn-off time of the light or the combination thereof through the light source, a time required for glucose detection is provided on one hand, and it is ensured that the light energy entering the eyeball is unable to cause any harm on the other hand. Then, step S104 may be selectively performed, by which before the light is transmitted into the eyeball, the light information of the light from the first beam splitter is detected, so as to perform a feedback control with the optical characteristic of the light. The light information comprises at least one of the energy information and the position information. The optical characteristic is, for example, a position for emitting energy and/or light. Next, in step S106, the light emitted from the light source is transmitted into the eyeball and focused on the eyeball through the first beam splitter with the focusing function such that a reflected light reflected from the eyeball is generated. Then, one of step S108 and step S110 may be performed. Wherein, in step S108, the reflected light reflected from the eyeball is transmitted to the set of photo detectors through the first beam splitter. In step S110, the reflected light reflected from the eyeball is transmitted to the second beam splitter through the first beam splitter, and then the reflected light is transmitted to the set of photo detectors through the second beam splitter. Furthermore, in step S112, the optical angular information and the absorption energy information of the reflected light transmitted to the set of photo detectors are measured by the set of photo detectors. Then, in step S114, the optical angular difference and the absorption energy difference between the light emitted from the light source and the reflected light transmitted to the set of photo detectors are calculated by processing the optical angular information and the absorption energy information. Next, in step S116, the optical angular difference and the absorption energy difference are analyzed to calculate the information of the biological molecule, wherein the biological molecule at least comprises the glucose, the glucose information is calculated through the biological molecule information, the glucose concentration in the eyeball (e.g., aqueous humor within eyeball) has a corresponding relationship with the corresponding concentration of blood glucose, the blood glucose information (e.g., concentration of blood glucose) is calculated using the corresponding relationship. The biological molecule is, for example, cholesterol, uric acid, water, lactic acid, urea, ascorbic acid, or a combination thereof. Moreover, the biological molecule may comprise an interference molecule therein, and the interference molecule is, for example, different from the measurement target (e.g., glucose), such as cholesterol, uric acid, water, lactic acid, urea, or ascorbic acid. Wherein, ascorbic acid and lactic acid may generate interference to the optical angular information whereas water may generate interference to the absorption energy information. Furthermore, in step S116, interference generated by the interference molecule may further be selectively removed. Variations of the method for non-invasive blood glucose monitoring and various used devices of the fifth exemplary embodiment have been described in detail in the first to the fourth exemplary embodiments, so that descriptions thereof are not repeated.

According to the above descriptions, in the method for non-invasive blood glucose monitoring of the fifth exemplary embodiment, since an optical eyeball detecting method is used to measure the glucose information (e.g., concentration of glucose) of the measuring object, the glucose information (e.g., glucose concentration) of the measuring object may be continuously obtained in real time, and since the glucose concentration has a relationship with a blood glucose concentration, the blood glucose information (e.g., concentration of blood glucose) may be read.

On the other hand, the above-mentioned exemplary embodiment of the apparatus for non-invasive glucose monitoring may further be used in the application of a portable mobile device, so that the portable mobile device has a non-invasive blood glucose monitoring function. The portable mobile device is, for example, mobile phone, tablet PC, digital camera, and so forth. The following descriptions below are, the exemplary embodiments, for describing a portable mobile device with a non-invasive blood glucose monitoring function.

Figure 6:
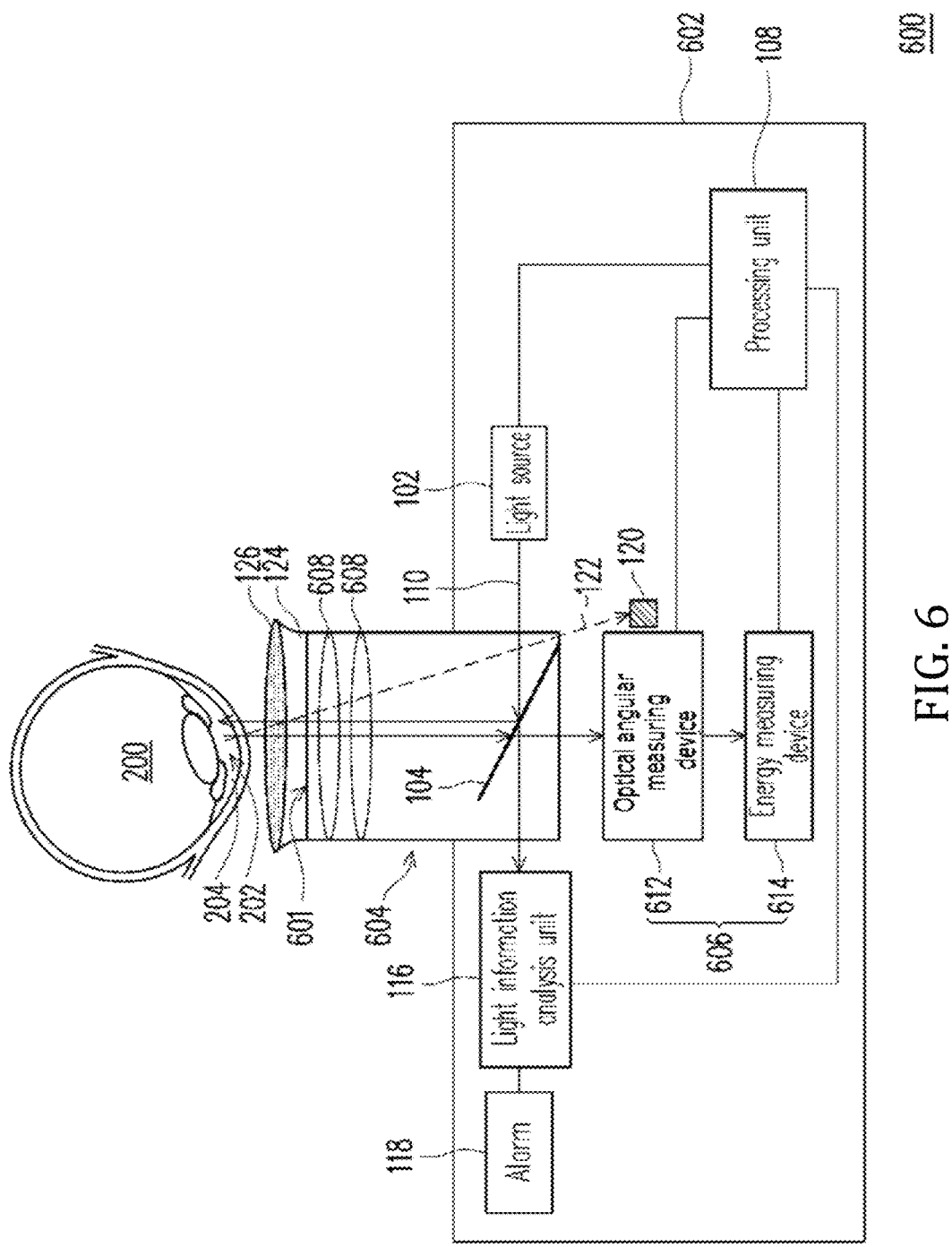
FIG. 6 is a schematic diagram illustrating a portable mobile device with a non-invasive blood glucose monitoring function in accordance with a sixth exemplary embodiment.

FIG. 6 is a schematic diagram illustrating a portable mobile device with a non-invasive blood glucose monitoring function in accordance with a sixth exemplary embodiment.

Referring to FIG. 2 and FIG. 6, a difference between a portable mobile device 600 of the sixth exemplary embodiment and the apparatus for non-invasive glucose monitoring 300 of the second exemplary embodiment is that the portable mobile device 600 further comprises a device body 602 and an optical kit 604. The optical kit 604 is disposed on the device body 602, and the optical kit 604 comprises the first beam splitter 104 therein. A set of photo detectors 606, the processing unit 108, the light source 102, the light information analysis unit 116, and the alarm 118 are, for example, disposed in the device body 602, but the disclosure is not limited thereto. Moreover, the set of photo detectors 606 comprises an optical angular measuring device 612 and an energy measuring device 614, wherein the portable mobile device 600 uses a light sensing element in a camera module thereof as the energy measuring device 614 in the set of photo detectors 606. The optical angular measuring device 612 and the energy measuring device 614 are, for example, respectively coupled to the processing unit 108, but the disclosure is not limited thereto. The optical angular measuring device 612 is, for example, an active optical angular measuring device or a passive optical angular measuring device. The energy measuring device 614 is, for example, a light sensing element, such as a charge coupled device, a complementary metal oxide semiconductor sensors or a light emitting diode. In addition, the light 110 used by the portable mobile device 600 for blood glucose monitoring is transmitted through a light route of the camera module of the portable mobile device 600. Compositions, coupling relations and functions of the other components of the portable mobile device 600 of the sixth exemplary embodiment are similar to that of the apparatus for non-invasive blood glucose monitoring 300 of the second exemplary embodiment, and the similar components of the portable mobile device 600 of the sixth exemplary embodiment and of the apparatus for non-invasive blood glucose monitoring 300 of the second exemplary embodiment are with similar compositions; furthermore, the method for blood glucose monitoring may be referred to the third exemplary embodiment, so that detailed descriptions thereof are not repeated.

Moreover, in the sixth exemplary embodiment, an end of the joint element 124 is connected to a light outlet 601 of the portable mobile device 600, and another end of the joint element 124 is used for resting on an outer corner of the eye.

On the other hand, the optical kit 604 may further selectively comprise a lens set 608. When the optical kit 604 has the lens set 608, the optical kit 604 may be integrated as a camera lens in camera module of the portable mobile device 600. In addition, whether or not the optical kit 604 has the lens set 608, the camera lens in the camera module of the portable mobile device 600 camera module may be replaced by the optical kit 604 in order to perform the blood glucose monitoring. In another exemplary embodiment, during the blood glucose monitoring, the optical kit 604, with the design of the light source, may be externally attached directly on the camera lens of the camera module of the portable mobile device 600.

In the present exemplary embodiment, the reflected light 111 emitted from the light source 102 is transmitted into the eyeball 200 and focused on the eyeball 200 through the first beam splitter 104. The set of photo detectors 606 is, for example, used to measure the reflected light 111 reflected from the eyeball 200 and then passed through or reflected from the first beam splitter 104. The reflected light 111 to be measured is first transmitted to the optical angular measuring device 612 for measuring the optical angular information, and then transmitted to the energy measuring device 614 for measuring the absorption energy information.

According to the above descriptions, the portable mobile device 600 of the sixth exemplary embodiment may simultaneously analyze the optical angular difference and the absorption energy difference between the light 110 emitted from the light source 102 and the reflected light 111 transmitted to the set of photo detectors 606, thus obtaining a glucose information (e.g., concentration of glucose), and since the concentration of glucose in the eyeball 200 (e.g., aqueous humor within eyeball) has a corresponding relationship with the corresponding concentration of blood glucose, a blood glucose information (e.g., concentration of blood glucose) with high accuracy is read through the corresponding relationship. In addition, since the blood glucose monitoring function is integrated to the portable mobile device 600, it is convenient in utilization. Moreover, telemedicine care may be provided by using the program or network of the portable mobile device 600 to connect to the cloud.

Figure 7:
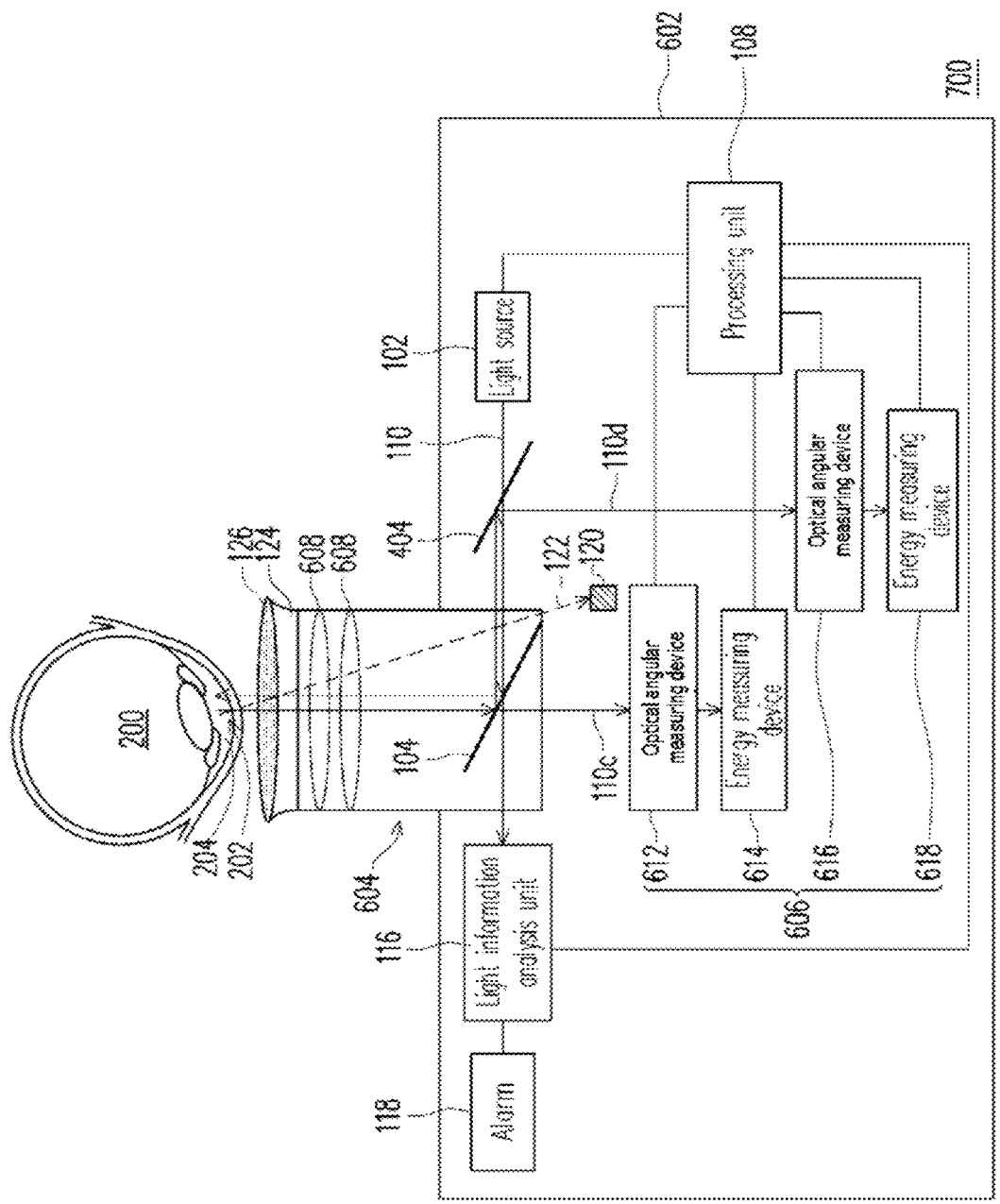
FIG. 7 is a schematic diagram illustrating a portable mobile device with a non-invasive blood glucose monitoring function in accordance with a seventh exemplary embodiment.

FIG. 7 is a schematic diagram illustrating a portable mobile device with a non-invasive blood glucose monitoring function in accordance with a seventh exemplary embodiment.

Referring to FIG. 6 and FIG. 7, a difference between a portable mobile device 700 of the seventh exemplary embodiment and the portable mobile device 600 of the sixth exemplary embodiment is that the portable mobile device 700 further comprises the second beam splitter 404 (may be referred to the third exemplary embodiment), and the set of photo detectors 606 further comprises an optical angular measuring device 616 and an energy measuring device 618. The optical angular measuring device 616 is, for example, an active optical angular measuring device or a passive optical angular measuring device. The energy measuring device 618 is, for example, a light sensing element, such as a charge coupled device, a complementary metal oxide semiconductor sensors or a light emitting diode. Compositions, coupling relations and functions of the other components of the portable mobile device 700 of the seventh exemplary embodiment are similar to that of the portable mobile device 600 of the sixth exemplary embodiment, and the similar components of the portable mobile device 700 of the seventh exemplary embodiment and of the portable mobile device 600 of the sixth exemplary embodiment are with similar compositions; furthermore, the method for blood glucose monitoring may be referred to the third exemplary embodiment, so that detailed descriptions thereof are not repeated.

The second beam splitter 404 is, for example, to transmit the reflected light 111 reflected from the eyeball 200 and then transmitted through the first beam splitter 104 to the set of photo detectors 606. The second beam splitter 404 is, for example, an optical film, an optical lens, an optical grating, a diffractive optic element, or a combination of any the above elements.

In the set of photo detectors 606, the optical angular measuring device 612 and the energy measuring device 614 are, for example, used for measuring a ray of reflected light 111c reflected from the eyeball 200 and then passed through the first beam splitter 104 reflected from the eyeball 200 and then passed through the first beam splitter 104. The reflected light 111c to be measured is, for example, first transmitted to the optical angular measuring device 612 for measuring the optical angular information, and then transmitted to the energy measuring device 614 for measuring the absorption energy. The optical angular measuring device 616 and the energy measuring device 618 are, for example, used for measuring a ray of reflected light 111d reflected from the eyeball 200, transmitted to the second beam splitter 404 through the first beam splitter 104 to the, and then reflect by the second beam splitter 404. The reflected light 111d to be measured is, for example, first transmitted to the optical angular measuring device 616 for measuring the optical angular information, and then transmitted to the energy measuring device 618 for measuring the absorption energy information.

In the present exemplary embodiment, the energy measuring devices 614, 618 are described as two separate components; however, in another exemplary embodiment, the energy measuring devices 614, 618 may be a plurality of different sensing regions on the same light sensing element and may also use the different sensing regions on the light sensing element to sense the light.

Similarly, the portable mobile device 700 of the seventh exemplary embodiment may simultaneously analyze the optical angular difference and the absorption energy difference between the light 110c emitted from the light source 102 and the reflected light 111c, 111d transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 700, it is convenient in utilization. Moreover, telemedicine care may be provided by using the program or network of the portable mobile device 700 to connect to the cloud.

Figure 8:
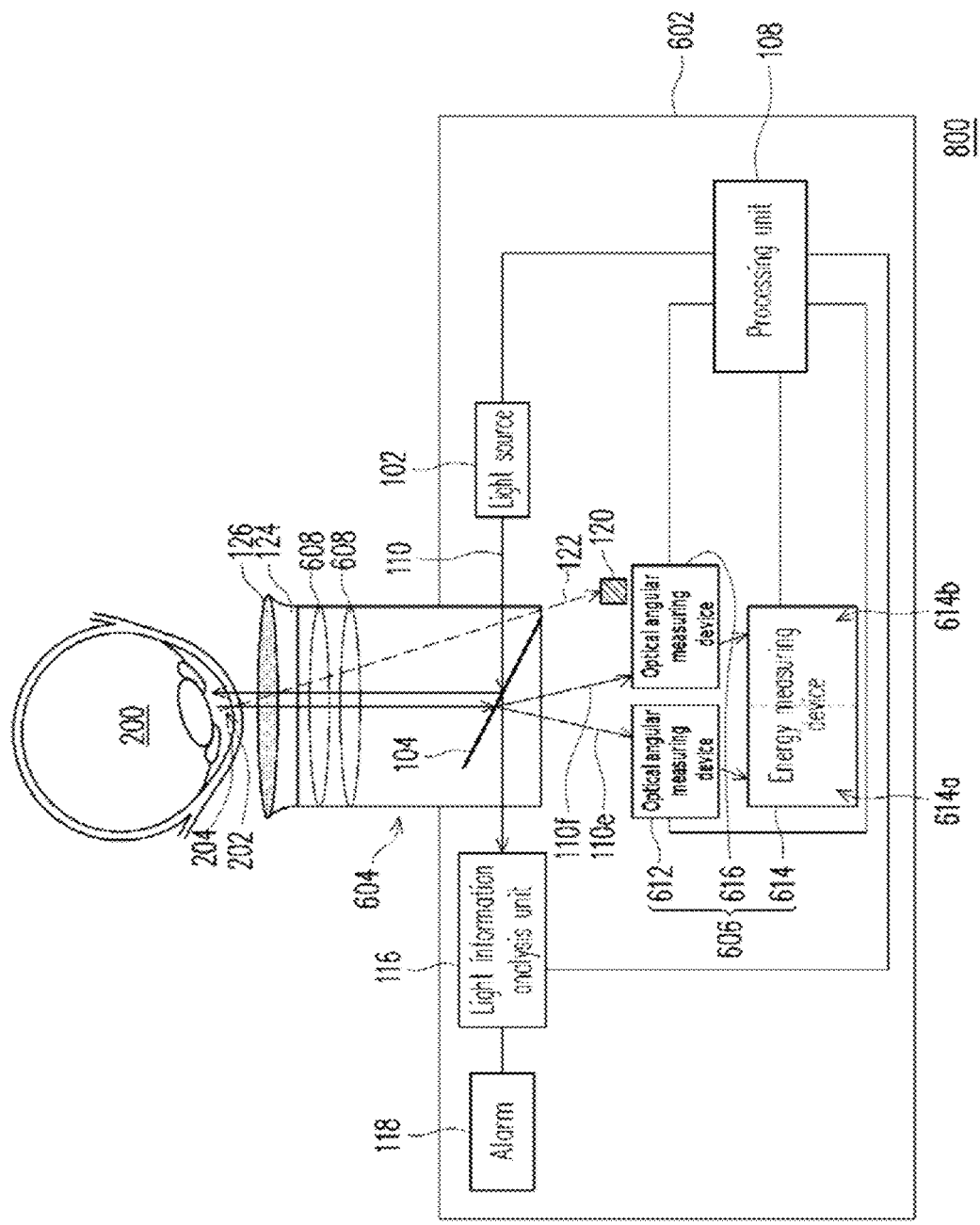
FIG. 8 is a schematic diagram illustrating a portable mobile device with a non-invasive blood glucose monitoring function in accordance with an eighth exemplary embodiment.

FIG. 8 is a schematic diagram illustrating a portable mobile device with a non-invasive blood glucose monitoring function in accordance with an eighth exemplary embodiment.

Referring to FIG. 7 and FIG. 8, a difference between a portable mobile device 800 of the eighth exemplary embodiment and the portable mobile device 700 of the seventh exemplary embodiment is that, in the portable mobile device 700, the light 110 may generate two rays of reflected light 111e, 111f after passed through the first beam splitter 104, thus not having the second beam splitter 404 in the portable mobile device 700. In addition, the set of photo detectors 606 of the portable mobile device 800 has only the energy measuring device 614 not the energy measuring device 618. The energy measuring device 614 comprises a plurality of sensing regions 614a, 614b, wherein the sensing regions 614a, 614b may respectively measure the absorption energy information of the reflected light 111e, 111f. Compositions, coupling relations and functions of the other components of the portable mobile device 800 of the eighth exemplary embodiment are similar to that of the portable mobile device 700 of the seventh exemplary embodiment, and the similar components in the eighth exemplary embodiment and in the seventh exemplary embodiment are with similar compositions; furthermore, the method for blood glucose monitoring may be referred to the seventh exemplary embodiment, so that detailed descriptions thereof are not repeated.

In the present exemplary embodiment, the same energy measuring device 614 is used to measure the reflected light 111e, 111f. However, in another exemplary embodiment, the portable mobile device 800 may also use two separate energy measuring devices to measure the reflected light 111e, 111f.

It is noted that, in the aforementioned exemplary embodiments, the reflected light 111 being divided into two rays of reflected light 111e, 111f by the first beam splitter 104 is taken as an example for the description, but the disclosure is not limited thereto. One of ordinary skill in the art would be able to know that, according to the above exemplary embodiments, when the reflected light 111 is divided into two or more rays of light by the first beam splitter 104, the number of the sensing regions on the energy measuring device 614 may also be divided into two or more, so as to respectively correspond to the light from the first beam splitter 104, and thus capable of measuring the absorption energy information of the corresponded light, respectively.

Although, in the present embodiment, the two or more rays of the light received by the energy measuring device 614 is generated by the first beam splitter 104, but the disclosure is not limited thereto. In another exemplary embodiment, the two or more rays of the light received by the energy measuring device 614 may also be formed by the light source 102; therefore, the light passed through the first beam splitter 104 may be more than two, and now the number of the sensing regions on the energy measuring device 614 may also be divided into more than two, so as to respectively correspond to the light from the first beam splitter 104, and thus capable of measuring the absorption energy information of the corresponded light, respectively.

Similarly, the portable mobile device 800 of the eighth exemplary embodiment may simultaneously analyze the optical angular difference and the absorption energy difference between the light 110 emitted from the light source 102 and the reflected light 111e, 111f transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 800, it is convenient in utilization. Moreover, telemedicine care may be provided by using the program or network of the portable mobile device 800 to connect to the cloud for using the real-time blood glucose data to remind or control medication and to directly inform the medical unit to perform first aid in case of emergency situation.

Figure 9:
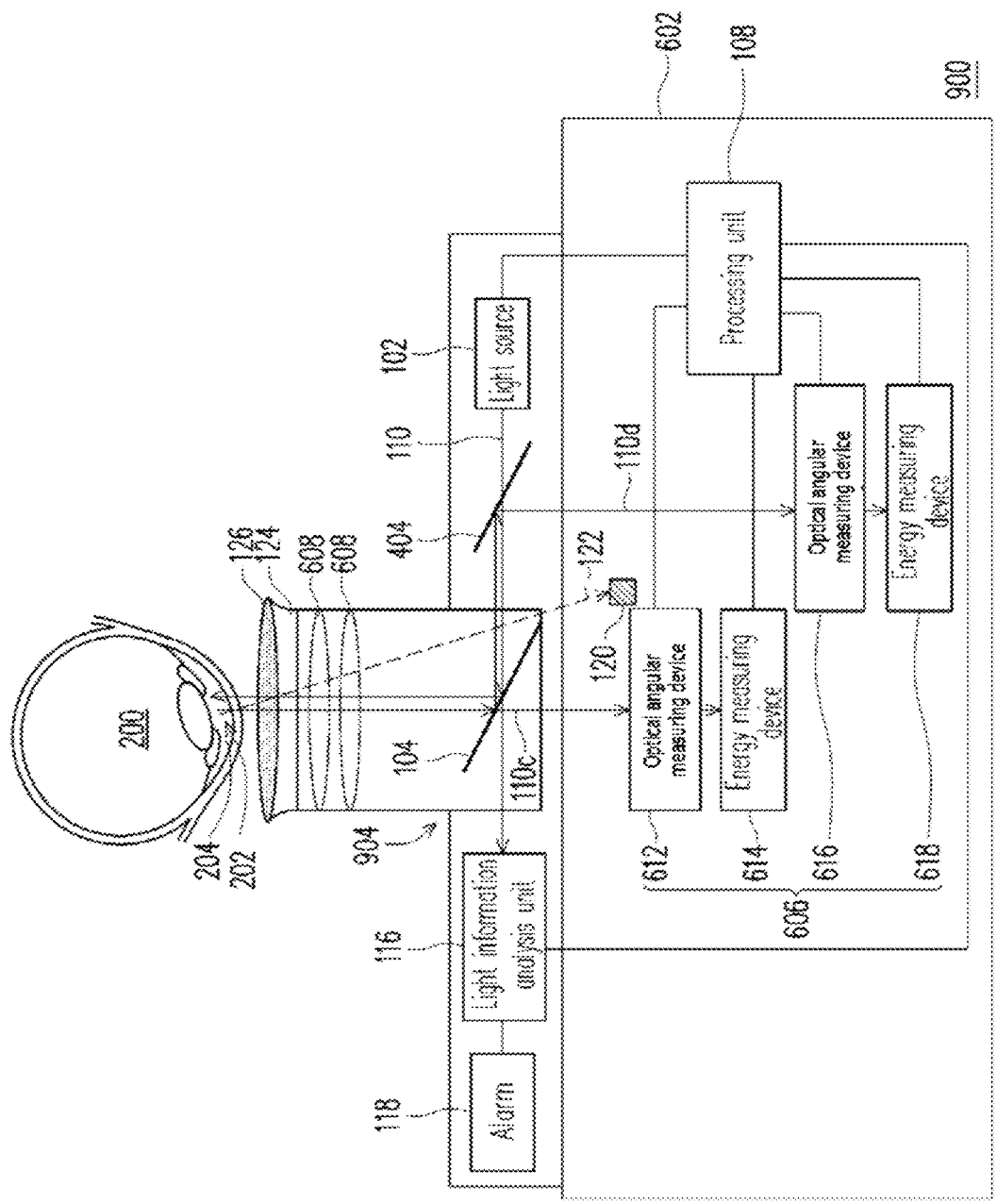
FIG. 9 is a schematic diagram illustrating a portable mobile device with a non-invasive blood glucose monitoring function in accordance with a ninth exemplary embodiment.

FIG. 9 is a schematic diagram illustrating a portable mobile device with a non-invasive blood glucose monitoring function in accordance with a ninth exemplary embodiment.

Referring to FIG. 7 and FIG. 9, a difference between a portable mobile device 900 of the ninth exemplary embodiment and the portable mobile device 700 of the seventh exemplary embodiment is that the composition of an optical kit 904 of the ninth exemplary embodiment is different from the composition of the optical kit 604 of the seventh exemplary embodiment. The optical kit 904 is externally attached and disposed on the device body 602, and the optical kit 904 other than comprises the first beam splitter 104 and the lens set 608, also comprises the light source 102 and the second beam splitter 404. In addition, the optical kit 904 may further selectively comprise the light information analysis unit 116 and the alarm 118. Compositions, coupling relations and functions of the other components of the portable mobile device 900 of the ninth exemplary embodiment are similar to that of the portable mobile device 700 of the seventh exemplary embodiment, and the similar components in the ninth exemplary embodiment and in the seventh exemplary embodiment are with similar compositions; furthermore, the method for blood glucose monitoring may be referred to the seventh exemplary embodiment, so that detailed descriptions thereof are not repeated.

Similarly, the portable mobile device 900 of the ninth exemplary embodiment may simultaneously analyze the optical angular difference and the absorption energy difference between the light 110 emitted from the light source 102 and the reflected light 111e, 111d transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 800, it is convenient in utilization. Moreover, telemedicine care may be provided by using the program or network of the portable mobile device 800 to connect to the cloud.

It is noted that the concept of the externally connected optical kit 904 of the portable mobile device 900 in the ninth exemplary embodiment may also be applied to the sixth to the eighth exemplary embodiment.

Figure 10:
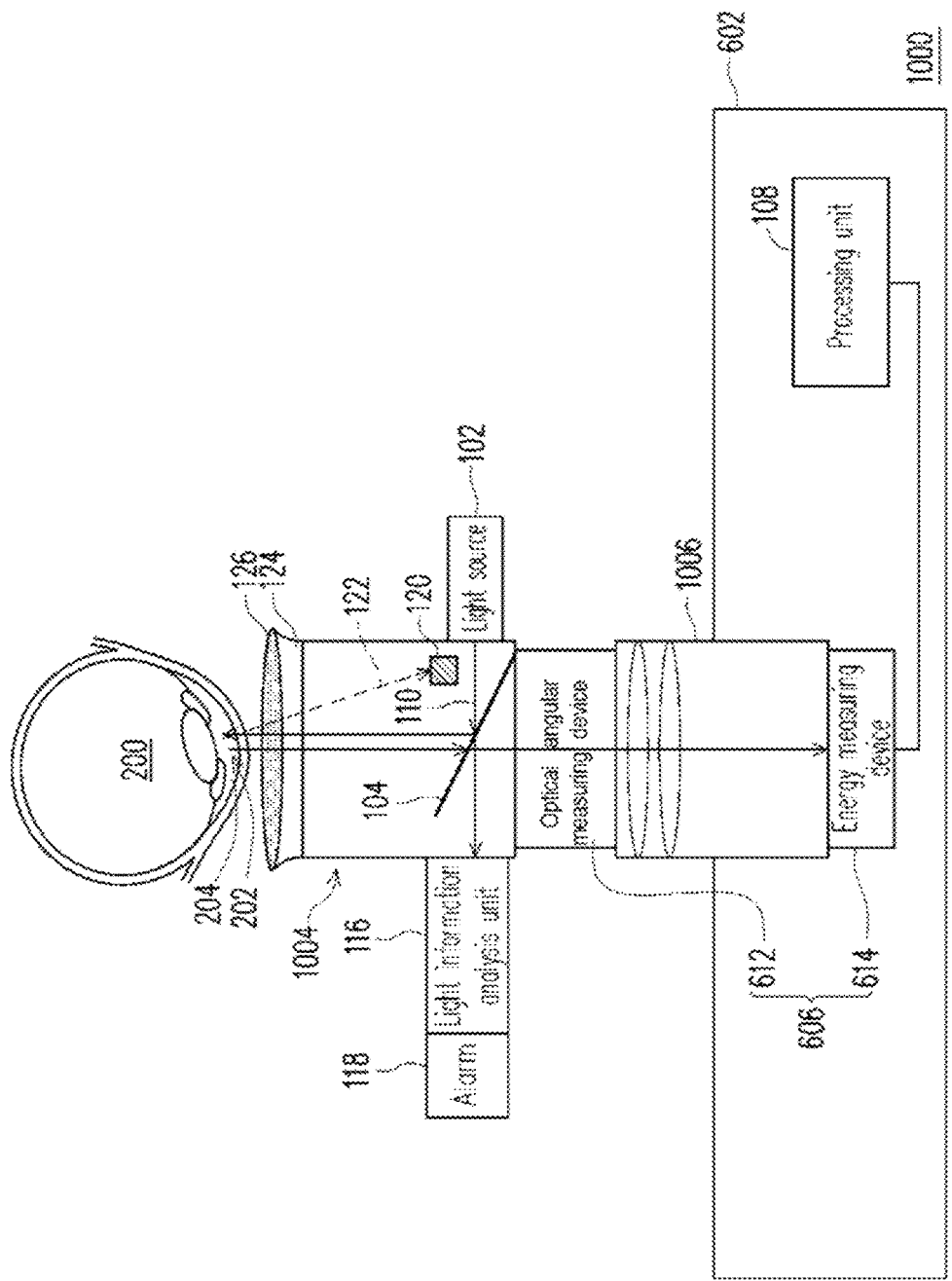
FIG. 10 is a schematic diagram illustrating a portable mobile device with a non-invasive blood glucose monitoring function in accordance with a tenth exemplary embodiment.

FIG. 10 is a schematic diagram illustrating a portable mobile device with a non-invasive blood glucose monitoring function in accordance with a tenth exemplary embodiment.

Referring to FIG. 6 and FIG. 10, a difference between a portable mobile device 1000 of the tenth exemplary embodiment and the portable mobile device 600 of the sixth exemplary embodiment is that the composition of an optical kit 1004 of the tenth exemplary embodiment is different from the composition of the optical kit 604 of the sixth exemplary embodiment. The optical kit 1004 is externally attached and disposed on a lens 1006 of the portable mobile device 1000, and the optical kit 1004 comprises the first beam splitter 104, the light source 102 and the optical angular measuring device 612. In addition, the optical kit 1004 may further selectively comprise the light information analysis unit 116 and the alarm 118. One of ordinary skill in the art would be able to couple the light source 102, the optical angular measuring device 612 and the light information analysis unit 116 with the processing unit 108 using the most suitable method, so that detailed descriptions are not repeated. Compositions, coupling relations and functions of the other components of the portable mobile device 1000 of the tenth exemplary embodiment are similar to that of the portable mobile device 600 of the sixth exemplary embodiment, and the similar components in the tenth exemplary embodiment and in the sixth exemplary embodiment are with similar compositions; furthermore, the method for blood glucose monitoring may be referred to the sixth exemplary embodiment, so that detailed descriptions thereof are not repeated.

When measuring the blood glucose, the optical angular measuring device 612 and the energy measuring device 614 are, for example, used to measure the reflected light 111 reflected from the eyeball 200 and then passed through the first beam splitter 104. The reflected light 111 to be measured is, for example, first transmitted to the optical angular measuring device 612 for measuring the optical angular information, and then transmitted to the energy measuring device 614, after passed through the lens 1006, for measuring the absorption energy information.

Similarly, the portable mobile device 1000 of the tenth exemplary embodiment may simultaneously analyze the optical angular difference and the absorption energy difference between the light 110 emitted from the light source 102 and the reflected light 111 transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 1000, it is convenient in utilization. Moreover, telemedicine care may be provided by using the program or network of the portable mobile device 1000 to connect to the cloud.

Figure 11:
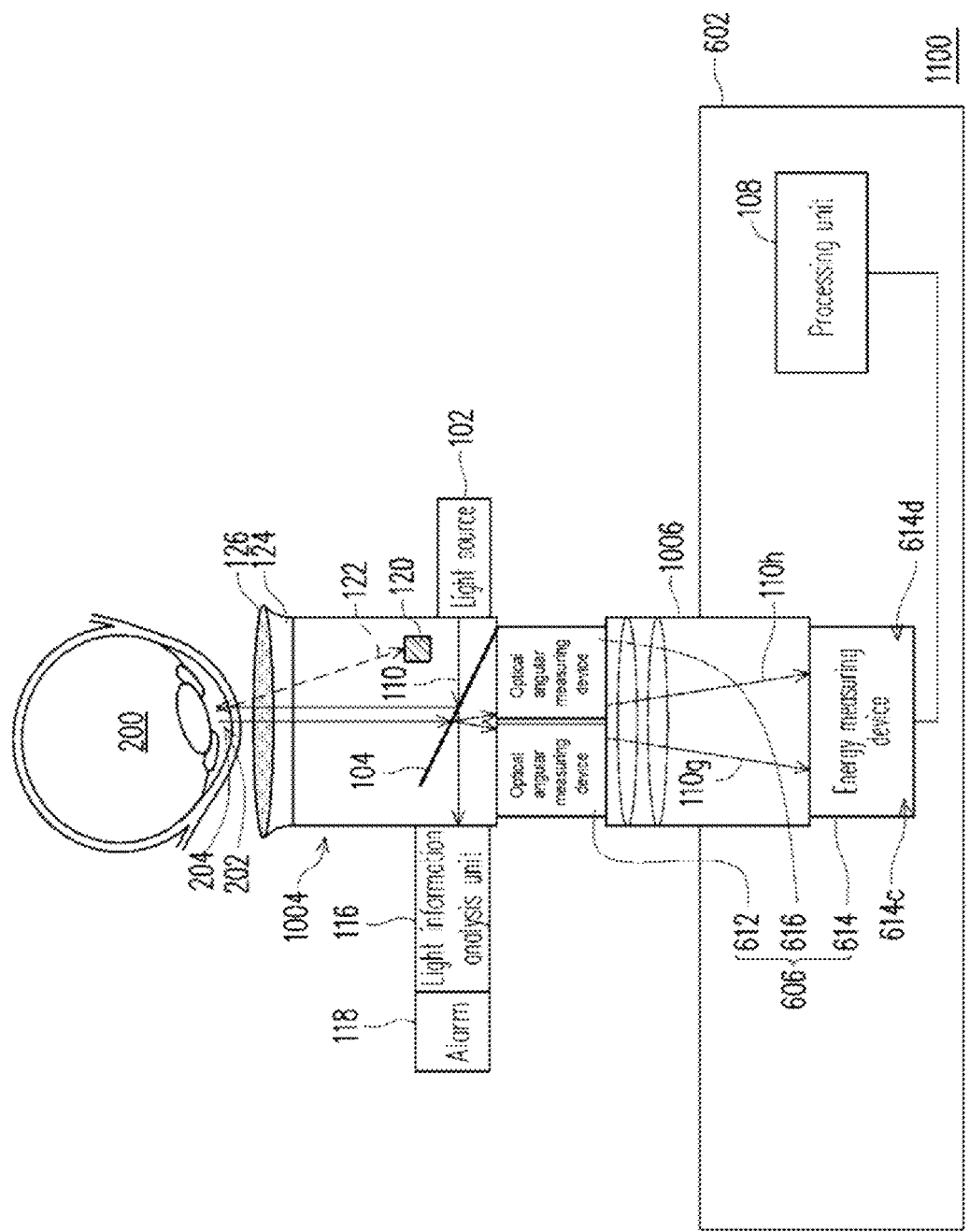
FIG. 11 is a schematic diagram illustrating a portable mobile device with a non-invasive blood glucose monitoring function in accordance with an eleventh exemplary embodiment.

FIG. 11 is a schematic diagram illustrating a portable mobile device with a non-invasive blood glucose monitoring function in accordance with an eleventh exemplary embodiment.

Referring to FIG. 10 and FIG. 11, a difference between a portable mobile device 1100 of the eleventh exemplary embodiment and the portable mobile device 1000 of the tenth exemplary embodiment is that, in the portable mobile device 1100, the reflected light 111 may generate two rays of reflected light 111g, 111h after passed through the first beam splitter 104. In addition, the set of photo detectors 606 of the portable mobile device 1100 comprises the optical angular measuring devices 612, 616 and the energy measuring device 614. Wherein, the energy measuring device 614 comprises the sensing regions 614c, 614d. The reflected light 111g, 111h may measure the optical angular information through the optical angular measuring devices 612, 616, respectively, and then measure the absorption energy information through the sensing regions 614c, 614d of the energy measuring device 614, respectively. Compositions, coupling relations and functions of the other components of the portable mobile device 1100 of the eleventh exemplary embodiment are similar to that of the portable mobile device 1000 of the tenth exemplary embodiment, and the similar components in the eleventh exemplary embodiment and in the tenth exemplary embodiment are with similar compositions; furthermore, the method for blood glucose monitoring may be referred to the tenth exemplary embodiment, so that detailed descriptions thereof are not repeated.

In the present exemplary embodiment, the portable mobile device 1100 may measure the reflected light 111g, 111h by the same energy measuring device 614. However, in another exemplary embodiment, the portable mobile device 1100 may also use two separate energy measuring devices to measure the reflected light 111g, 111h.

It is noted that, in the aforementioned exemplary embodiments, the reflected light 111 being divided into two rays of reflected light 111g, 111h by the first beam splitter 104 is taken as an example for the description, but the disclosure is not limited thereto. One of ordinary skill in the art would be able to know that, according to the above exemplary embodiments, when the reflected light 111 can be divided into two or more rays of reflected light 111g, 111h by the first beam splitter 104, the number of sensing regions on the energy measuring device 614 may also be divided into two or more, so as to respectively correspond to the light from the first beam splitter 104, and thus capable of respectively measuring the absorption energy information of the corresponded light.

Although, in the present exemplary embodiment, the two or more rays of the light received by the energy measuring device 614 is generated by the first beam splitter 104, but the disclosure is not limited thereto. In another exemplary embodiment, the two or more rays of the light received by the energy measuring device 614 may also be formed by the light source 102; therefore, the light passed through the first beam splitter 104 may be more than two, and now the number of sensing regions on the energy measuring device 614 may also be divided into more than two, so as to respectively correspond to the light from the first beam splitter 104, and thus capable of respectively measuring the absorption energy information of the corresponded light.

Similarly, the portable mobile device 1100 of the eleventh exemplary embodiment may simultaneously analyze the optical angular difference and the absorption energy difference between the light 110 emitted from the light source 102 and the reflected light 111g, 111h transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 1100, it is convenient in utilization. Moreover, telemedicine care may be provided by using the program or network of the portable mobile device 1100 to connect to the cloud.

Figure 12:
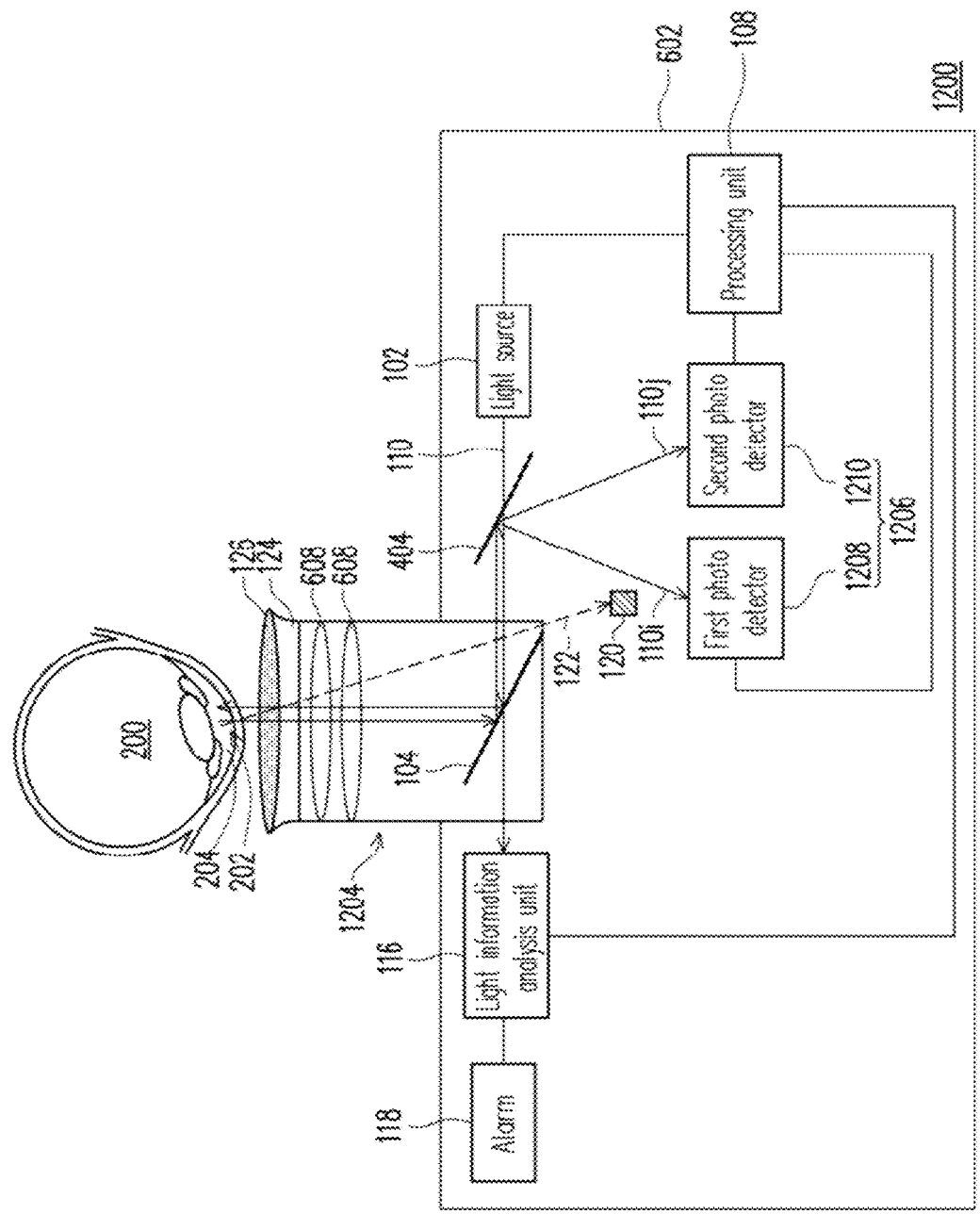
FIG. 12 is a schematic diagram illustrating a portable mobile device with a non-invasive blood glucose monitoring function in accordance with a twelfth exemplary embodiment.

FIG. 12 is a schematic diagram illustrating a portable mobile device with a non-invasive blood glucose monitoring function in accordance with a twelfth exemplary embodiment.

Referring to FIG. 7 and FIG. 12, a difference between a portable mobile device 1200 of the twelfth exemplary embodiment and the portable mobile device 700 of the seventh exemplary embodiment is that, in the portable mobile device 1200, the reflected light 111 may generate two rays of reflected light 111i, 111j after passed through the second beam splitter 404. In addition, a set of photo detectors 1206 of the portable mobile device 1200 comprises a first photo detector 1208 and a second photo detector 1210, and the first photo detector 1208 and the second photo detector 1210 are located at a same side of the second beam splitter 404. In the present exemplary embodiment, the first photo detector 1208 and the second photo detector 1210 are, for example, located at the side of the second beam splitter 404 where the reflected light 111 is reflect from, and are respectively used to measure two rays of reflected light 111i, 111j generated by reflecting the reflected light 111 through the second beam splitter 404. Wherein, one of the first photo detector 1208 and the second photo detector 1210 is, for example, the optical angular measuring device for measuring the optical angular information, and another of the first photo detector 1208 and the second photo detector 1210 is, for example, the measuring device for measuring the absorption energy information. In other exemplary embodiment, the first photo detector 1208 and the second photo detector 1210 may also comprise the optical angular measuring device and the energy measuring device, respectively. The first photo detector 1208 and the second photo detector 1210 are, for example, coupled to the processing unit 108, but the discourse is not limited thereto. Compositions, coupling relations and functions of the other components of the portable mobile device 1200 of the twelfth exemplary embodiment are similar to that of the portable mobile device 700 of the seventh exemplary embodiment, and the similar components in the twelfth exemplary embodiment and in the seventh exemplary embodiment are with similar compositions; furthermore, the method for blood glucose monitoring may be referred to the fourth exemplary embodiment, so that detailed descriptions thereof are not repeated.

In another example embodiment, the first photo detector 1208 and the second photo detector 1210 may be also located at the side of the second beam splitter 404 where the reflected light 111 passes there through, and are respectively used to measure reflected light 111a, 111b generated by the reflected light 111 after passed through the second beam splitter 404.

Similarly, the portable mobile device 1200 of the twelfth exemplary embodiment may simultaneously analyze the optical angular difference and the absorption energy difference between the light 110 emitted from the light source 102 and the reflected light 111i, 111g transmitted to the set of photo detectors 1206, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 1200, it is convenient in utilization. Moreover, telemedicine care may be provided by using the program or network of the portable mobile device 1000 to connect to the cloud for using the real-time blood glucose data to remind or control medication and to directly inform the medical unit to perform first aid in case of emergency situation.

Figure 13:
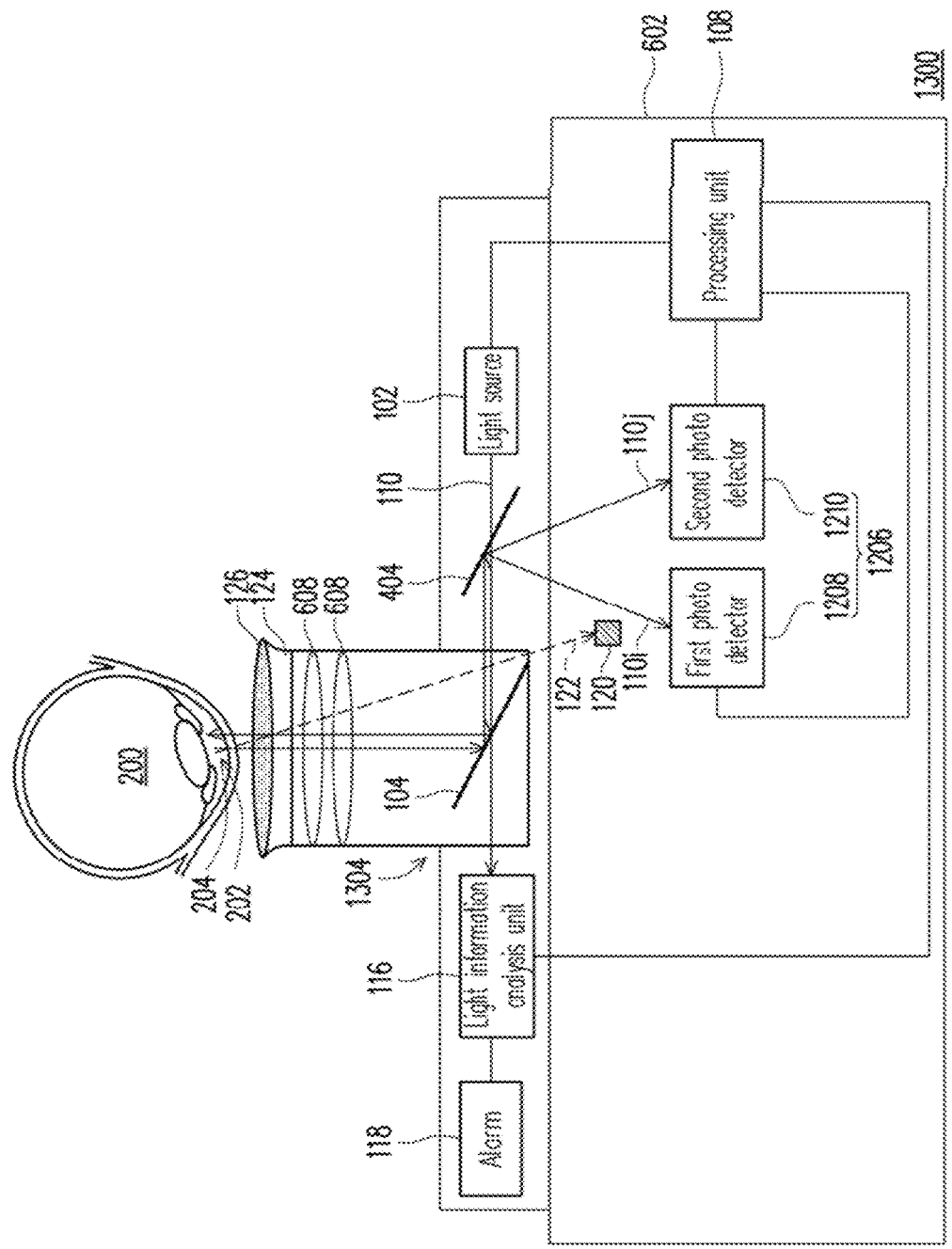
FIG. 13 is a schematic diagram illustrating a portable mobile device with a non-invasive blood glucose monitoring function in accordance with a thirteenth exemplary embodiment.

FIG. 13 is a schematic diagram illustrating a portable mobile device with a non-invasive blood glucose monitoring function in accordance with a thirteenth exemplary embodiment.

Referring to FIG. 12 and FIG. 13, a difference between a portable mobile device 1300 of the thirteenth exemplary embodiment and the portable mobile device 1200 of the twelfth exemplary embodiment is that the composition of an optical kit 1304 of the thirteenth exemplary embodiment is different from the composition of an optical kit 1204 of the twelfth exemplary embodiment. The optical kit 1304 is externally attached and disposed on the device body 602, and the optical kit 1304 other than comprises the first beam splitter 104 and the lens set 608, also comprises the light source 102 and the second beam splitter 404. In addition, the optical kit 904 may further selectively comprise the light information analysis unit 116 and the alarm 118. Compositions, coupling relations and functions of the other components of the portable mobile device 1300 of the thirteenth exemplary embodiment are similar to that of the portable mobile device 1200 of the twelfth exemplary embodiment, and the similar components in the thirteenth exemplary embodiment and in the twelfth exemplary embodiment are with similar compositions; furthermore, the method for blood glucose monitoring may be referred to the twelfth exemplary embodiment, so that detailed descriptions thereof are not repeated.

Similarly, the portable mobile device 1300 of the thirteenth exemplary embodiment may simultaneously analyze the optical angular difference and the absorption energy difference between the light 110 emitted from the light source 102 and the reflected light 111i 111j transmitted to the set of photo detectors 606, thus obtaining the glucose information (e.g., concentration of glucose), and since the concentration of glucose in the eyeball 200 (e.g., aqueous humor within eyeball) has a corresponding relationship with the concentration of blood glucose, the blood glucose information (e.g., concentration of blood glucose) with high accuracy is read through the corresponding relationship. In addition, since the blood glucose monitoring function is integrated to the portable mobile device 1300, it is convenient in utilization. Moreover, telemedicine care may be provided by using the program or network of the portable mobile device 1300 to connect to the cloud.

In addition, although the apparatus for non-invasive glucose monitoring used in the application of portable mobile device described the sixth to the thirteenth exemplary embodiments are taken as examples for the descriptions, but the disclosure is not limited thereto. One of ordinary skill in the art would able to refer to the portable mobile device with a non-invasive blood glucose monitoring function disclosed in the sixth to the thirteenth exemplary embodiment to combine the concept of the portable mobile device with a non-invasive blood glucose monitoring function with the various implementations of the first to the fourth exemplary embodiments, so as to produce a diversified portable mobile device with a non-invasive blood glucose monitoring function.

Moreover, although the first to the thirteenth exemplary embodiments use the examples of measuring a single eye for the descriptions, but the disclosure is not limited thereto. One of ordinary skill in the art would be able to know the method for applying the contents of the present disclosure to both two eyes according the aforementioned exemplary embodiments.

Figure 14:
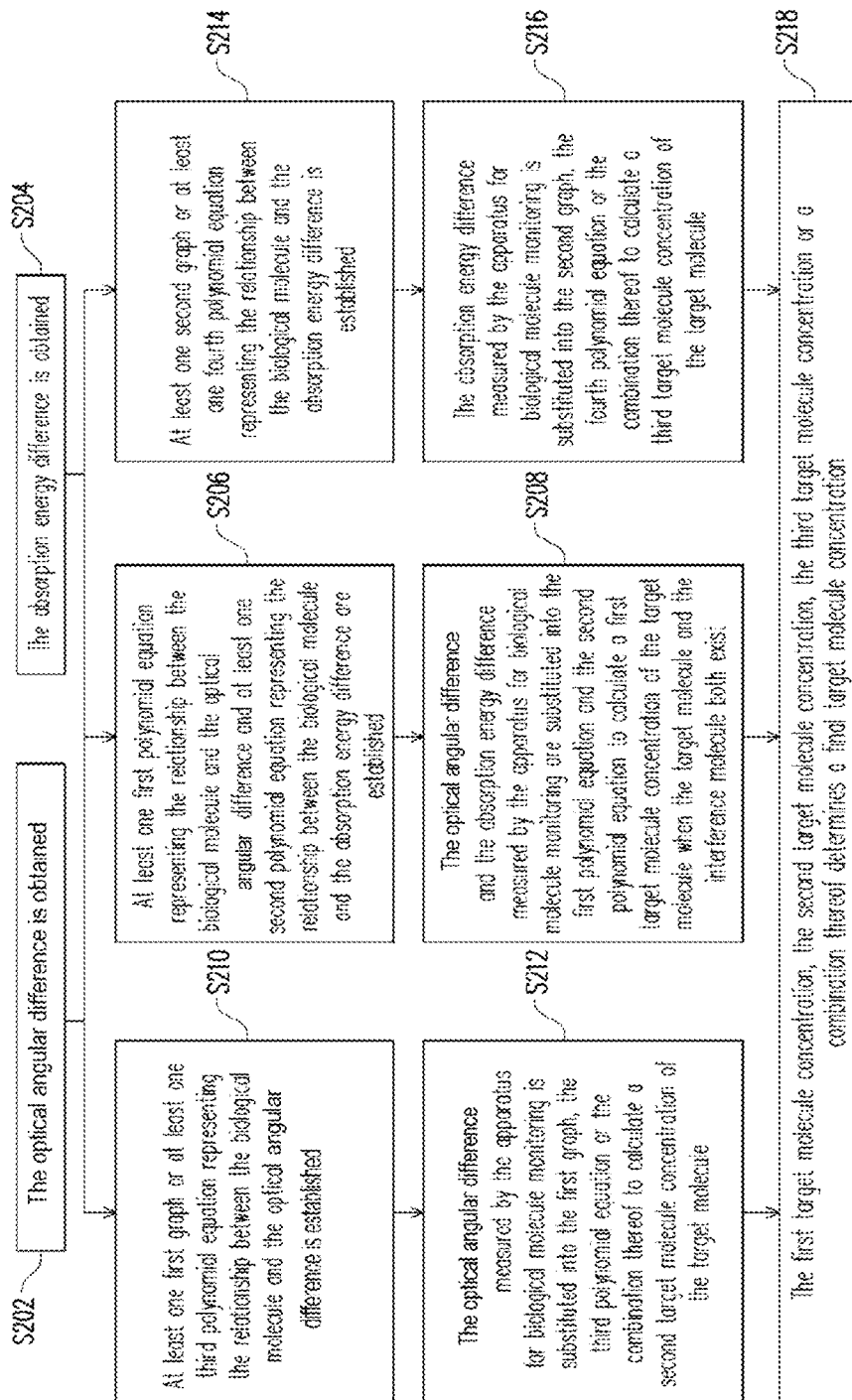
FIG. 14 is a schematic diagram illustrating a method for analyzing biological molecule in accordance with a fourteenth exemplary embodiment.

FIG. 14 is a schematic diagram illustrating a method for analyzing biological molecule in accordance with a fourteenth exemplary embodiment.

The method for analyzing biological molecule in the present embodiment, for example, performs analyzing through the processing unit of an apparatus for biological molecule monitoring. The biological molecule, such as glucose, cholesterol, uric acid, water, lactic acid, urea, ascorbic acid or a combination thereof is analyzed.

Referring to FIG. 14, step S202 may be performed to obtain the optical angular difference. A method for obtaining the optical angular difference comprises the following steps. Firstly, a portion of a plurality of optical angular difference values that exceeded an acceptable variation range measured by the apparatus for biological molecule monitoring is discarded. Then, at least one mathematical statistical method is used to calculate the optical angular difference values. Wherein, the mathematical statistical method is, for example, a least square error regression analysis method. The acceptable variation range is, for example, the range represented by the following listed mathematical formulas.

The acceptable variation range for the optical angular difference=the arithmetic mean of the optical angular difference values×(1±15%).

In addition, step S204 may be performed to obtain the absorption energy difference. A method for obtaining the absorption energy difference comprises the following steps. Firstly, a portion of a plurality of absorption energy difference values that exceeded the acceptable variation range measured by the apparatus for biological molecule monitoring is discarded. Then, at least one mathematical statistical method is used to calculate the absorption energy difference values. Wherein, the mathematical statistical method is, for example, a least square error regression analysis method. The acceptable variation range is, for example, the range represented by the following listed mathematical formulas.

The acceptable variation range for the absorption energy difference=the arithmetic mean of the absorption energy difference values×(1±15%).

Step S206 is performed to establish at least one first polynomial equation representing the relationship between the biological molecule and the optical angular difference, and at least one second polynomial equation representing the relationship between the biological molecule and the absorption energy difference. Wherein, the biological molecule comprises a target molecule and at least one interference molecule, and a plurality of variables of the first polynomial equation and the second polynomial equation respectively comprise the target molecule concentration and the interference molecule concentration variables.

The first polynomial equation is, for example, established from a plurality of biological molecule concentration values and a plurality of corresponding optical angular difference values stored in a database. The second polynomial equation is, for example, established from a plurality of biological molecule concentration values and a plurality of corresponding absorption energy difference values stored in the database. Wherein, a plurality of samples of the biological molecule concentration values stored in the database comprises a plurality of live samples or a plurality of standard samples.

In addition, the steps of establishing the first polynomial equation and the second polynomial equation further comprise distinguishing between a plurality of optical angular difference ranges and a plurality of absorption energy difference ranges, having the first polynomial equation correspondingly used in each of the optical angular difference ranges, and having the second polynomial equation correspondingly used in each of the absorption energy ranges.

For example, when the target molecule is the glucose and the interference molecule is the lactic acid, and three optical angular difference ranges and three absorption energy difference ranges are distinguished, the selected first polynomial equation and second polynomial equation are shown below, but the disclosure is not limited thereto.

The first polynomial equation corresponded to the first optical angular difference range:

$$\theta_{(glucose\ effect+lactic\ acid\ effect)} = a_1 X_{glucose\ concentration} + b_1 Y_{lactic\ acid\ concentration} + c_1$$

The first polynomial equation corresponded to the second optical angular difference range:

$$\theta_{(glucose\ effect+lactic\ acid\ effect)} = a_1' X_{glucose\ concentration} + b_1' Y_{lactic\ acid\ concentration} + c_1'$$

The first polynomial equation corresponded to the third optical angular difference range:

$$\theta_{(glucose\ effect+lactic\ acid\ effect)} = a_1'' X_{glucose\ concentration} + b_1'' Y_{lactic\ acid\ concentration} + c_1''$$

wherein, $\theta_{(glucose\ effect+lactic\ acid\ effect)}$ is the optical angular difference, $X_{glucose\ concentration}$ is the target molecule concentration variable, $Y_{lactic\ acid\ concentration}$ is the interference molecule concentration variable, $a_1$, $a_1'$, $a_1''$, $b_1$, $b_1'$, $b_1''$, $c_1$, $c_1'$ and $c_1''$ are the known coefficients.

The second polynomial equation corresponded to the first absorption energy difference range:

$$P_{(glucose\ effect+lactic\ acid\ effect)} = a_2 X_{glucose\ concentration} + b_2 Y_{lactic\ acid\ concentration} + c_2$$

The second polynomial equation corresponded to the second absorption energy difference range:

$$P_{(glucose\ effect+lactic\ acid\ effect)} = a_2' X_{glucose\ concentration} + b_2' Y_{lactic\ acid\ concentration} + c_2'$$

The second polynomial equation corresponded to the third absorption energy difference range:

$$P_{(glucose\ effect+lactic\ acid\ effect)} = a_2'' X_{glucose\ concentration} + b_2'' Y_{lactic\ acid\ concentration} + c_2''$$

wherein, $P_{(glucose\ effect+lactic\ acid\ effect)}$ is the absorption energy difference, X glucose concentration is the target molecule concentration variable, $Y_{lactic\ acid\ concentration}$ is the interference molecule concentration variable, $a_2$, $a_2'$, $a_2''$, $b_2$, $b_2'$, $b_2''$, $c_2$, $c_2'$ and $c_2''$ are the known coefficients.

Step S208 is performed, by which the optical angular difference and the absorption energy difference measured by the apparatus for biological molecule monitoring are substituted into the first polynomial equation and the second polynomial equation to calculate a first target molecule concentration of the target molecule which simultaneously exists in the target molecule and the interference molecule. A method for calculating the first target molecule concentration is, for example, solving the simultaneous equations of the first polynomial equation and the second polynomial equation. During the process of performing step S208, the optical angular difference and the absorption energy difference are analyzed by controlling the change factor, in order to obtain the first target molecule concentration. Wherein, the change factor comprises a light emitting frequency, a light energy intensity, a length of turn-on time of the light, a length of turn-off time of the light, an opto-element offset, or a combination thereof.

In addition, steps S210, S212, S214, S216, S218, or a combination thereof may be performed selectively.

In step S210, at least one first graph or at least one third polynomial equation representing the relationship between the biological molecule and the optical angular difference is established. Wherein, the variable of the third polynomial equation comprises the target molecule concentration variable.

The first graph and the third polynomial equation, for example, are established from the biological molecule concentration values stored in the database and the corresponding optical angular difference values. Wherein, the samples of the biological molecule concentration stored in the database comprise a plurality of live samples or a plurality of standard samples.

In addition, the steps of establishing the first graph or the third polynomial equation further comprise distinguishing a plurality of optical angular difference ranges, having the first graph, the third polynomial equation, or the combination thereof correspondingly used in each of the optical angular difference ranges.

For example, when the target molecule is the glucose and three optical angular difference ranges are distinguished, the selected third polynomial equation is shown below, but the disclosure is not limited thereto.

The third polynomial equation corresponded to the first optical angular difference range:

$$\theta_{(glucose\ effect)} = a_3 X_{glucose\ concentration} + c_3$$

The third polynomial equation corresponded to the second optical angular difference range:

$$\theta_{(glucose\ effect)} = a_3' X_{glucose\ concentration} + c_3'$$

The third polynomial equation corresponded to the third optical angular difference range:

$$\theta_{(glucose\ effect)} = a_3'' X_{glucose\ concentration} + c_3''$$

wherein, $\theta_{(glucose\ effect)}$ is the optical angular difference, $X_{glucose\ concentration}$ is the target molecule concentration variable, $a_3$, $a_3'$, $a_3''$, $c_3$, $c_3'$ and $c_3''$ are the known coefficients.

In step S212, the optical angular difference measured by the apparatus for biological molecule monitoring is substituted into the first graph, the third polynomial equation or the combination thereof to calculate a second target molecule concentration of the target molecule. During the process of performing step S212, the optical angular difference is analyzed by controlling the change factor, in order to obtain the second target molecule concentration. Wherein, the change factor comprises the light emitting frequency, the light energy intensity, the length of turn-on time of the light, the length of turn-off time of the light, the opto-element offset, or the combination thereof.

In step S214, at least one second graph or at least one fourth polynomial equation representing the relationship between the biological molecule and the absorption energy difference is established. Wherein, the variable of the fourth polynomial equation comprises the target molecule concentration variable.

The second graph and the fourth polynomial equation, for example, are established from the biological molecule concentration values and the corresponding absorption energy difference values stored in the database. Wherein, the samples of the biological molecule concentration stored in the database comprise a plurality of live samples or a plurality of standard samples.

In addition, the steps of establishing the second graph or the fourth polynomial equation further comprise distinguishing a plurality of absorption energy difference ranges, having the second graph, the fourth polynomial equation, or the combination thereof correspondingly used in each of the absorption energy difference ranges.

For example, when the target molecule is the glucose and three absorption energy difference ranges are distinguished, the selected fourth polynomial equation is shown below, but the disclosure is not limited thereto.

The fourth polynomial equation corresponded to the first absorption energy difference range:

$$P_{(glucose\ effect)} = a_4 X_{glucose\ concentration} + c_4$$

The fourth polynomial equation corresponded to the second absorption energy difference range:

$$P_{(glucose\ effect)} = a_4' X_{glucose\ concentration} + c_4'$$

The fourth polynomial equation corresponded to the third absorption energy difference range:

$$P_{(glucose\ effect)} = a_4'' X_{glucose\ concentration} + c_4''$$

wherein, $P_{(glucose\ effect)}$ is the absorption energy difference, $X_{glucose}$ concentration is the target molecule concentration variable, $a_4$, $a_4'$, $a_4''$, $c_4$, $c_4'$ and $c_4''$ are the known coefficients.

In step S216, the absorption energy difference measured by the apparatus for biological molecule monitoring is substituted into the second graph, the fourth polynomial equation or the combination thereof to calculate a third target molecule concentration of the target molecule. During the process of performing step S216, the absorption energy difference is analyzed by controlling the change factor, in order to obtain the third target molecule concentration. Wherein, the change factor comprises the light emitting frequency, the light energy intensity, the length of turn-on time of the light, the length of turn-off time of the light, the opto-element offset, or the combination thereof.

In step S218, the first target molecule concentration, the second target molecule concentration, the third target molecule concentration or a combination thereof determines a final target molecule concentration. In other embodiments, when the step S218 is not performed, the first target molecule concentration obtained through the step S208 may be used as the final target molecule concentration.

According to the fourteenth embodiment, the analysis method of the above-mentioned biological molecule may obtain the target molecule concentration, which simultaneously exists in the target molecule and the interference molecule through the optical angular difference values and the absorption energy difference values; therefore, a more accurate concentration of target molecule may be obtained.

To improve the light utilization efficiency, the light source in any one of the abovementioned exemplary embodiments may be further partially or entirely packaged in an optical module. Similarly, each of the photo detectors in any one of the abovementioned exemplary embodiments may be further partially or entirely packaged in an optical module. Optical elements may be applied in the optical module or in the optical path of the apparatus (or portable mobile device) to converge the light beam. Exemplary embodiments of the apparatus for glucose monitoring having optical packaged modules are described with reference to FIGS. 15A-28B.

Figure 15:
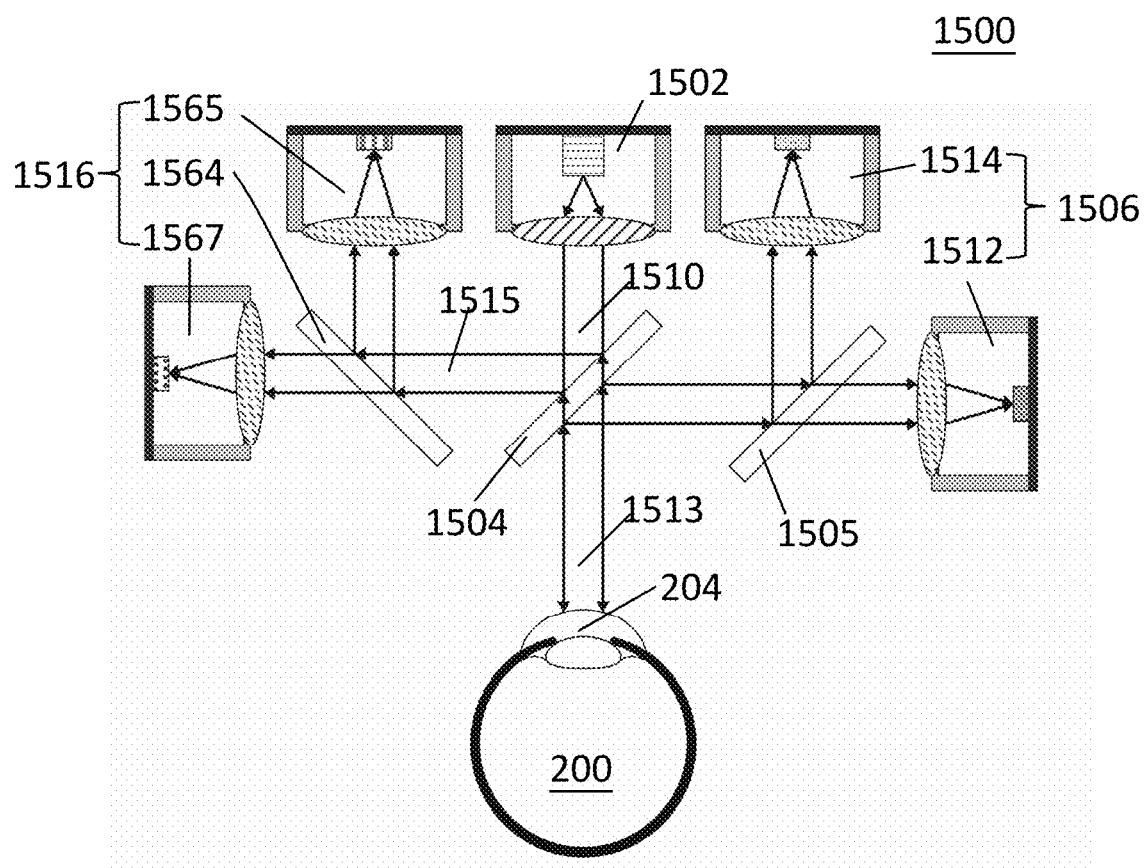
FIG. 15 is a schematic diagram illustrating an apparatus for non-invasive glucose monitoring in accordance with a fifteenth exemplary embodiment.

FIG. 15 illustrates an apparatus for non-invasive glucose monitoring in accordance with a fifteenth exemplary embodiment of the present disclosure. The apparatus 1500 includes a light source module 1502, a first beam splitter 1504, a second beam splitter 1505, a set of light detecting modules 1506, and a light information analysis unit 1516.

As shown in FIG. 15, the light source module 1502 generates a light beam 1510. The light beam 1510 is split into a first light beam 1513 and a second light beam 1515 by the first beam splitter 1504. In the present exemplary embodiment, the first light beam 1513 is a part of the light beam 1510 that passes through the first beam splitter 1504 and enters into an eyeball 200 of an object, while the second light beam 1515 is a part of the light beam 1510 that is reflected by the first beam splitter 1504 and then detected by the light information analysis unit 1516. To obtain glucose information of the eyeball 200, light reflected by the eyeball 200, particularly by the anterior chamber of the eyeball 200, is reflected to the second beam splitter 1505 by the first beam splitter 1504 and then measured by the set of light detecting modules 1506. The glucose information of the eyeball 200 may be calculated by information obtained by the set of light detecting modules 1506 and the light information analysis unit 1516.

In the present exemplary embodiment as shown in FIG. 15, the light reflected by the eyeball 200 is reflected by the first beam splitter 1504 toward the second beam splitter 1505, and the light splits to two parts by the second beam splitter 1505. The two parts of the light split by the second beam splitter 1505 are detected by a set of light detecting modules 1506. The set of light detecting modules 1506 includes a first light detecting module 1512 and a second light detecting module 1514. One part of the light passes through the second beam splitter 1505 and is detected by the first light detecting module 1512; the other part of the light is reflected by the second beam splitter 1505 and is detected by the second light detecting module 1514. The first light detecting module 1512 may be configured to measure optical angular information of the light passed through the second beam splitter 1505. The optical angular information may be the angle of the major polarization axis of the reflected light with regarding to the angle of the major polarization axis of the emitted light. In some embodiments, a polarizer or a Faraday rotator may be coupled to the first light detecting module 1512 to measure the optical angular information. The second light detecting module 1514 may be configured to measure energy information of the light reflected by the second beam splitter 1505. The energy information may be a light power intensity of the reflected light with regarding to the light power intensity of the emitted light. The light power at a predetermined wavelength or at a predetermined range of wavelength.

Referring to the exemplary embodiment shown in FIG. 15, the second light detecting module 1514 may have a similar construction to the first light detecting module 1512. The photo detector of the second light detecting module 1514 may be different from the photo detector 1532 of the first light detecting module 1512, in order to measure different optical information of received light reflected by the second beam splitter 1505. The collimating element applied in the second light detecting module 1514 may have the same optical characteristics as the collimating element 1535 of the first light detecting module 1512. However, depending on optical properties and function of the photo detector, the collimating element applied in the second light detecting module 1514 may have different optical characteristics from the collimating element 1535 of the first light detecting module 1512. Other details of the second light detecting module 1514 are similar to those relevant to the first light detecting module 1512 mentioned hereinabove.

In the present exemplary embodiment, the light information analysis unit 1516 is configured for detecting light information of the second light beam 1515, which is the part of the light beam 1510 reflected by the first beam splitter 1504. Referring to FIG. 15, the light information analysis unit 1516 includes a third beam splitter 1564, a third light detecting module 1565, and a fourth light detecting module 1567. The second light beam 1515 is split into two parts by the third beam splitter 1564, one part of the light is reflected by the third beam splitter 1564 and is detected by the third light detecting module 1565. The other part of the light passes through the third beam splitter 1564 and is detected by the fourth light detecting module 1567. The third light detecting module 1565 may be configured to measure optical angular information of the light reflected by the third beam splitter 1564. The fourth light detecting module 1567 may be configured to measure energy information of the light passing through the third beam splitter 1564. The light information obtained by the light information analysis unit 1516 may be applied to acquire position information of the light, whereby detecting phase shifting of the light beam 1510.

As shown in FIG. 15, each of the third light detecting module 1565 and the fourth light detecting module 1567 may have a similar construction to the first light detecting module 1512, that is, a packaged optical module having a collimating element to direct received light toward a photodetector. Briefly, the third light detecting module 1565 and the fourth light detecting module 1567 may have a photo detector, such as an optical power meter or an optical sensor, mounted on a substrate and surrounded by a peripheral side wall, and a collimating element configured to confine the light transmitted by the third beam splitter 1564 toward the photo detector. Details of the third light detecting module 1565 and the fourth light detecting module 1567 are similar to abovementioned features of the first light detecting module 1512.

The apparatus 1500 may further include a processing unit (not shown) and an alarm (not shown). The processing unit may be coupled to the light source module 1502, the first light detecting module 1512, the second light detecting module 1514, and the light information analysis unit 1516. The processing unit is configured to execute instructions to control optical properties of the light beam 1510 and to calculate the glucose information according to the detected light information. The alarm may be coupled to the light information analysis unit 1516, which may send a light or a sound warning signal when the energy of the light beam 1510 is too high. Details of these and many other essential components or functional units of the apparatus for glucose monitoring are mentioned in previous embodiments hereinabove.

Figure 16A:
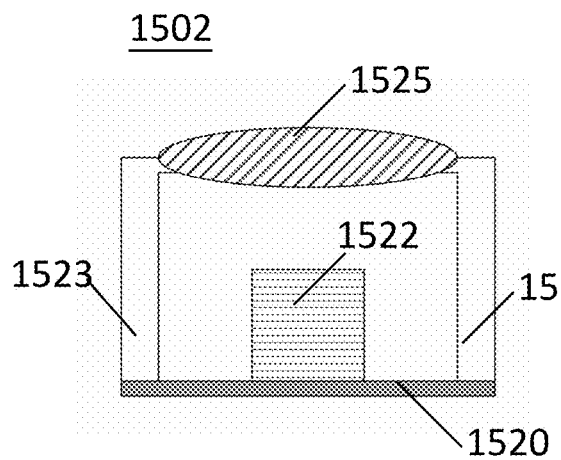
FIG. 16A and FIG. 16B respectively show schematic diagrams of a top view and an oblique sectional view of the light source module of the apparatus of FIG. 15 in accordance with the fifteenth exemplary embodiment.
Figure 16B:
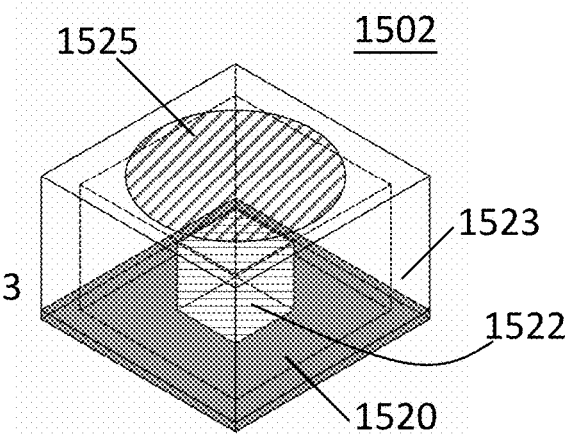

FIG. 16A and FIG. 16B provide schematic diagrams of a top view and an oblique sectional view, respectively, of the light source module 1502 used in the apparatus 1500 of the fifteenth embodiment. The light source module 1502 includes a substrate 1520, at least one light emitting element 1522 and a peripheral side wall 1523 mounted on the substrate 1520, and a collimating element 1525 configured for narrowing light emitted by the light emitting element 1522.

Figure 17:
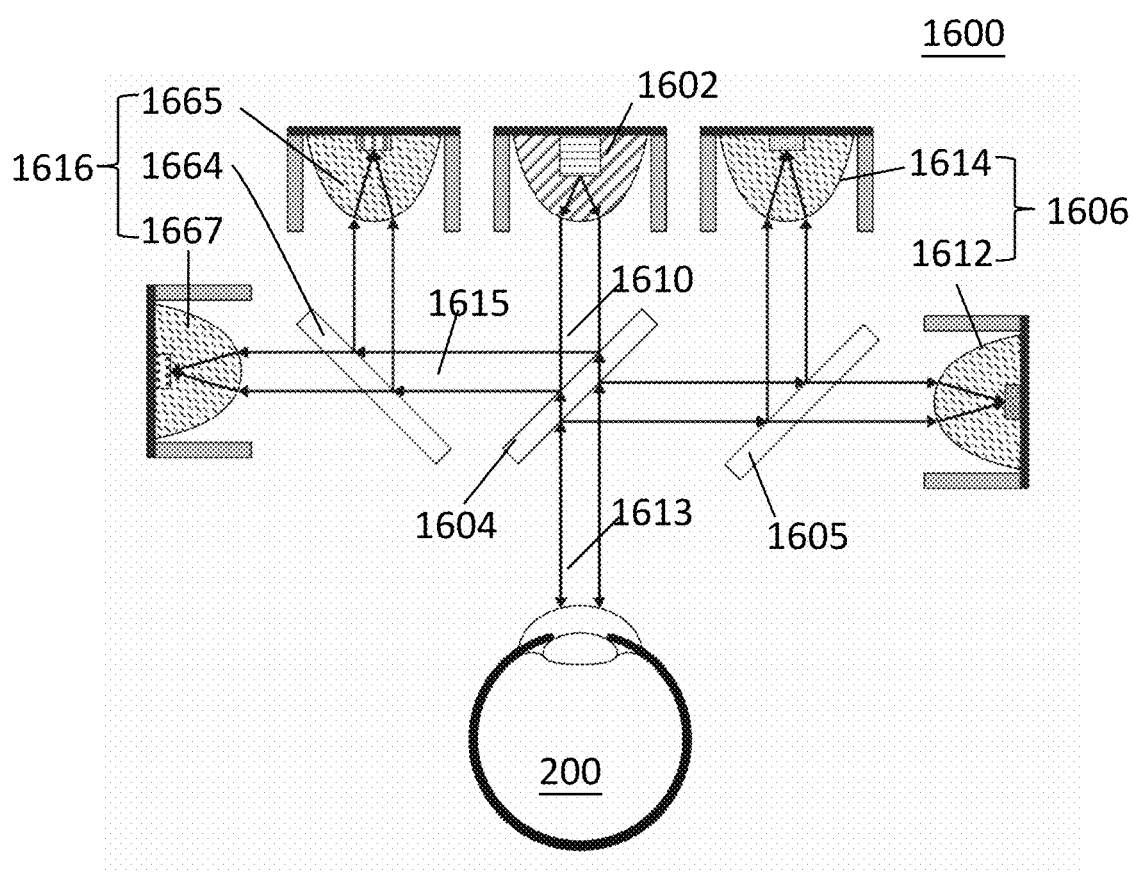
FIG. 17 is a schematic diagram illustrating an apparatus for non-invasive glucose monitoring in accordance with a sixteenth exemplary embodiment.

In FIG. 17, the substrate 1520 may include a printed circuit board (PCB) electrically coupled to the light emitting element 1522. The light emitting element 1522 may be a light emitting diode (LED) or a laser diode. The light emitting element 1522 is surrounded by the peripheral side wall 1523, which may confine the direction of light generated by the light source module 1502 and may prevent the generated light from being interfered by ambient stray light.

In the apparatus 1500, the collimating element 1525 is positioned between the light emitting element 1522 and the first beam splitter 1504 to narrow the emitted light. The collimating element 1525 may make the direction of the emitted light become more aligned in a specific direction (i.e., provide collimated light or parallel rays). The collimating element 1525 may make the spatial cross section of the emitted light become smaller. In the present exemplary embodiment, the collimating element 1525 is a collimating lens fixed to an end of the peripheral side wall 1523 away from the substrate 1520. It can be understood that the collimating element 1525 may be arranged in the optical path between the light emitting element 1522 and the first beam splitter 1504 by other means. For example, the light source module 1502 may further include a cover, which may be connected to the end of the peripheral side wall 1523 away from the substrate 1520, and the collimating element 1525 may be provided to an internal surface or an external surface of the cover. It can be understood that the collimating element 1525 may not be necessarily arranged in the light source module 1502, it may be positioned between the light source module 1502 and the first beam splitter 1504 in the apparatus 1500. Using such a light source module 1502, the light emitted by the light emitting element 1522 is confined by the collimating element 1525, providing the light beam 1510 to the first beam splitter 1504. It is contemplated that the collimating element 1525 may be a converging lens, such as a biconvex lens, a plano-convex lens or a meniscus lens. Furthermore, a focusing control mechanism may be coupled between the collimating element 1525 and the light emitting element 1522.

Figure 16C:
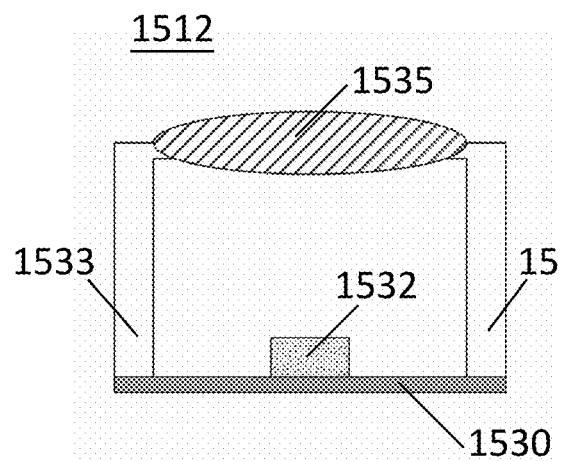
FIG. 16C and FIG. 16D respectively show schematic diagrams of a top view and an oblique sectional view of the first light detecting module of the apparatus of FIG. 15 in accordance with the fifteenth exemplary embodiment.
Figure 16D:
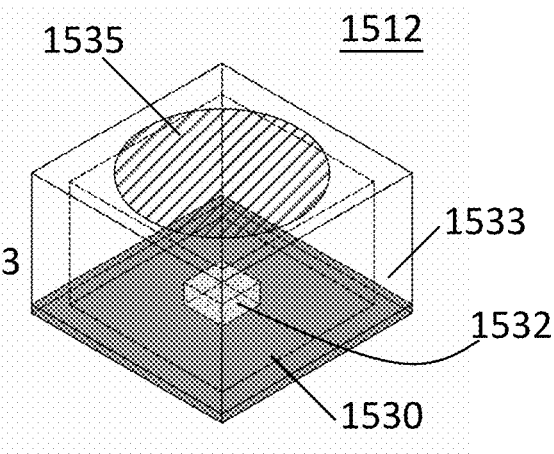

FIG. 16C and FIG. 16D provide schematic diagrams of a top view and an oblique sectional view, respectively, of the first light detecting module 1512. To improve the light receiving efficiency, the first light detecting module 1512 and the second light detecting module 1514 are also constructed to packaged optical modules having collimating elements to converge received light. The first light detecting module 1512 includes a substrate 1530, at least one photo detector 1532 and a peripheral side wall 1533 mounted on the substrate 1530, and a collimating element 1535 configured to direct the light transmitted by the second beam splitter 1505 toward the photo detector 1532.

The substrate 1530 may include a printed circuit board (PCB) electrically coupled to the photo detector 1532. The photo detector 1532 is surrounded by the peripheral side wall 1533, which may reduce ambient stray light received by the photo detector 1532. The collimating element 1535 is arranged between the photo detector 1532 and the second beam splitter 1505 in the apparatus 1500. The collimating element 1535 may make the direction of the light transmitted by the second beam splitter 1505 become more aligned in a direction toward the photo detector 1532 (i.e., provide collimated light or parallel rays). The collimating element 1535 may make the spatial cross section of the light transmitted by the second beam splitter 1505 becomes smaller. In the present exemplary embodiment, the collimating element 1525 is a collimating lens fixed to an end of the peripheral side wall 1533 away from the substrate 1530. It can be understood that the collimating element 1535 of the apparatus 1500 may be arranged in the optical path between the photo detector 1532 and the second beam splitter 1505 by other means.

FIG. 17 is a schematic diagram illustrating an apparatus for non-invasive glucose monitoring in accordance with a sixteenth exemplary embodiment of the present disclosure. The apparatus 1600 includes a light source module 1602 generating a light beam 1610, a first beam splitter 1604, a second beam splitter 1605, a set of light detecting modules 1606, and a light information analysis unit 1616. The set of light detecting modules 1606 includes a first light detecting module 1612 and a second light detecting module 1614. The light information analysis unit 1616 includes a third beam splitter 1664, a third light detecting module 1665, and a fourth light detecting module 1667. The optical path of the apparatus 1600 for glucose monitoring is substantially similar to the apparatus 1500 of the fifteenth exemplary embodiment, thus the main functional components of the apparatus 1600 and their arrangement are not described further for brevity.

Figure 18A:
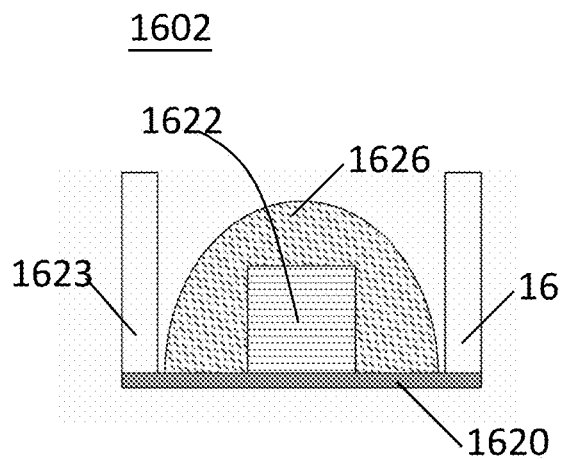
FIG. 18A and FIG. 18B respectively show schematic diagrams of a top view and an oblique sectional view of the light source module of the apparatus of FIG. 17 in accordance with the sixteenth exemplary embodiment.
Figure 18B:
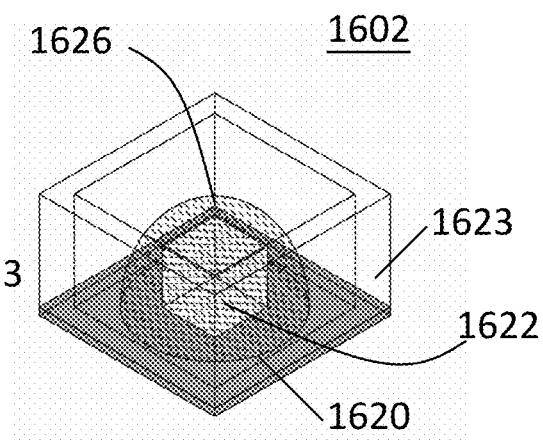

FIG. 18A and FIG. 18B provide a top view and an oblique sectional view, respectively, of the light source module 1602 used in the apparatus 1600 of the sixteenth embodiment. The light source module 1602 includes a substrate 1620, at least one light emitting element 1622 mounted on the substrate 1620, an encapsulant 1626 formed over the light emitting element 1622, and a peripheral side wall 1623 mounted on the substrate 1620 and surrounding the encapsulant 1626. Details of the substrate 1620, the light emitting element 1622, and the peripheral side wall 1623 of the present exemplary embodiment are similar to those of the fifteenth exemplary embodiment mentioned hereinabove.

The encapsulant 1626 is configured to converge light emitted by the light emitting element 1622. The encapsulant 1626 should be, at least partially, transparent so as to be an adequate medium for light propagation. The material of the encapsulant 1626 may be selected from silicone compounds or transparent polymeric materials. The transparent polymeric materials for producing the encapsulant 1626 may be polydimethylsiloxane (PDMS), polycarbonate (PC), or polymethyl methacrylate (PMMA). The encapsulant 1626 may seal the light emitting element 1622 to increase durability of the light emitting element 1622.

Moreover, the encapsulant 1626 is configured to improve the light extraction efficiency of the light source module 1602. In the present embodiment, the encapsulant 1626 has a substantially domed shape to reduce total internal reflection at the encapsulant/environment interface. In other embodiments, the encapsulant may have a hemispherical shape, a trapezoid shape, a cuboid shape, a spherical segment shape, a circular truncated cone shape, or any other irregular shape. The encapsulant 1626 may have a refractive index between a greater refractive index of the light emitting element (such as an LED semiconductor) and a low refractive index of the environmental medium (such as air). The encapsulant 1626 may be constructed in one single layer or multiple layers. For the encapsulant 1626 having multiple layers, each layer may have a different refractive index and refractive indices of the multiple layers may decrease gradually in a direction away from the substrate 1620. Total internal reflection of the emitted light is thus reduced by gradually reducing the high refractive index difference between the light emitting element 1622 and the environmental medium, thereby improving the light extraction efficiency.

Figure 18C:
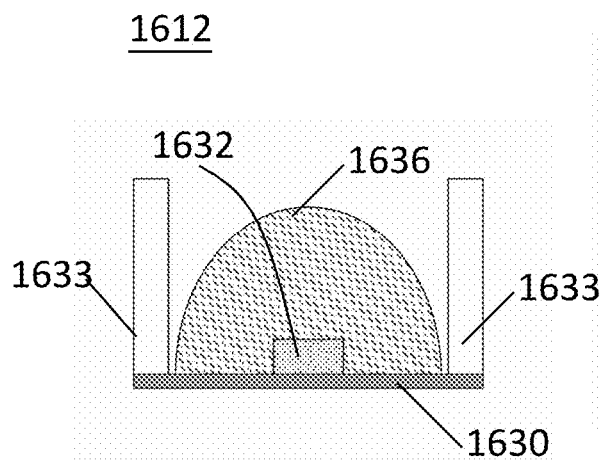
FIG. 18C and FIG. 18D respectively show schematic diagrams of a top view and an oblique sectional view of the first light detecting module of the apparatus of FIG. 17 in accordance with the sixteenth exemplary embodiment.
Figure 18D:
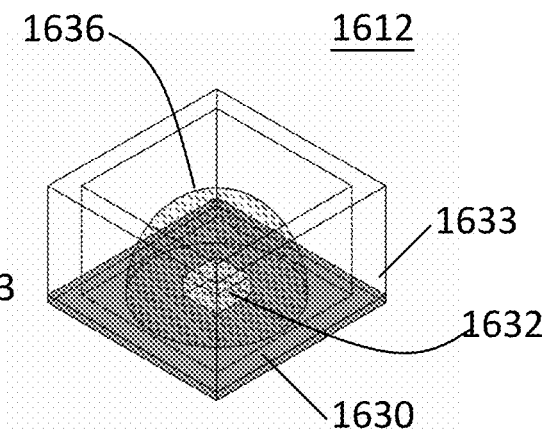

To improve the light receiving efficiency, each of the light detecting modules (1612, 1614, 1665, and 1667) may also be constructed as a packaged optical module, which includes an encapsulant sealing a photo detector. Taking the first light detecting module 1612 as an example, FIG. 18C and FIG. 18D provide a top view and an oblique sectional view, respectively, of the first light detecting module 1612 applied in the apparatus 1600 of the sixteenth embodiment. The first light detecting module 1612 includes a substrate 1630, at least one photo detector 1632 mounted on the substrate 1630, an encapsulant 1636 formed over the photo detector 1632, and a peripheral side wall 1633 mounted on the substrate 1630 and surrounding the encapsulant 1636. The encapsulant 1636 is configured to concentrate light toward the photodetector 1632, improving the light receiving efficiency of the first light detecting module 1612. Other details of each part of the first light detecting module 1612 are similar to those of the light source module 1602 mentioned hereinabove.

Figure 19:
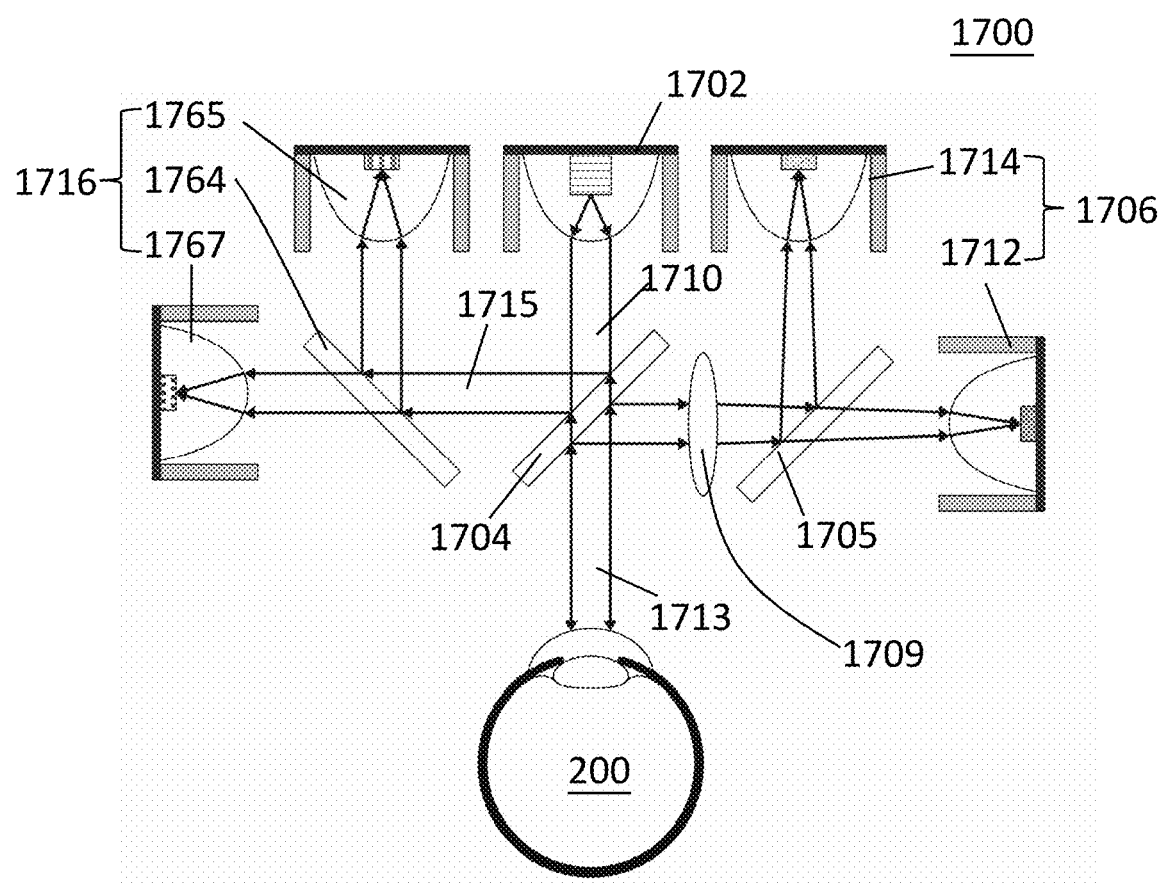
FIG. 19 is a schematic diagram illustrating an apparatus for non-invasive blood glucose monitoring in accordance with a seventeenth exemplary embodiment.

FIG. 19 is a schematic diagram illustrating an apparatus for non-invasive glucose monitoring in accordance with a seventeenth exemplary embodiment of the present disclosure. The apparatus 1700 includes a light source module 1702, a first beam splitter 1704, a converging lens 1709, a second beam splitter 1705, a set of light detecting modules 1706, and a light information analysis unit 1716. The set of light detecting modules 1706 includes a first light detecting module 1712 and a second light detecting module 1714. The light information analysis unit 1816 includes a third beam splitter 1764, a third light detecting module 1765, and a fourth light detecting module 1767.

Referring to FIG. 19, the light source module 1702 generates a light beam 1710. The light beam 1710 is split into a first light beam 1713 that passes through the first beam splitter 1704 and a second light beam 1715 that is reflected by the first beam splitter 1704.

The first light beam 1713 enters into an eyeball 200, whereby generating reflected light from the eyeball 200. The reflected light from the eyeball 200 is again reflected by the first beam splitter 1704, passes through the converging lens 1709, and is split into two parts by the second beam splitter 1705. One part of the light that passes through the second beam splitter 1705 is detected by the first light detecting module 1712; the other part of the light that is reflected by the second beam splitter 1705 is detected by the second light detecting module 1714. The first light detecting module 1712 may be configured to measure optical angular information of received light, while the second light detecting module 1714 may be configured to measure energy information of received light. In the present exemplary embodiment, the converging lens 1709 may be bi-convex or planoconvex, thus the beam of light passing through the converging lens 1709 converges to a spot around a photo detector of the first light detecting module 1712. The converging lens 1709 lies in the optical path between the first beam splitter 1704 and the second beam splitter 1705, converging the reflected light from the eyeball 200 toward the second beam splitter 1705, and thereby improving the light receiving efficiency of the first light detecting module 1712 and the second light detecting module 1714.

The second light beam 1715 is split into two parts by the third beam splitter 1764. One part of the light that is reflected by the third beam splitter 1764 is detected by the third light detecting module 1765; the other part of the light that passes through the third beam splitter 1764 is detected by the fourth light detecting module 1767. The third light detecting module 1765 may be configured to measure optical angular information of the light reflected by the third beam splitter 1764. The fourth light detecting module 1767 may be configured to measure energy information of the light passing through the third beam splitter 1764. The light information obtained by the light information analysis unit 1716 may be used to acquire position information of the light, thus shifting of the light beam 1710 would be noticed.

In the present exemplary embodiment shown in FIG. 19, the light source module 1702 is constructed to a packaged optical module with an encapsulant sealing a light emitting element to improve the light extraction efficiency, similar to the example shown in FIG. 18A and FIG. 18B. Each of the light detecting modules is also constructed to a packaged optical module with an encapsulant sealing a photo detector to improve the light receiving efficiency, similar to the example shown in FIG. 18C and FIG. 18C. Details of the packaged optical module and the encapsulant are as mentioned above.

According to the apparatus 1700 for glucose monitoring, the converging lens 1709 is provided together with the packaged optical modules (i.e. the light source module 1702 and the four light detecting modules) with encapsulants sealing the light emitting/detecting elements. It can be understood that the converging lens 1709 may be applied in any other apparatus having a first beam splitter and a second beam splitter in the abovementioned embodiments (for example, the fourth embodiment shown in FIG. 4) to improve the light receiving efficiency of the photo detectors.

Figure 20:
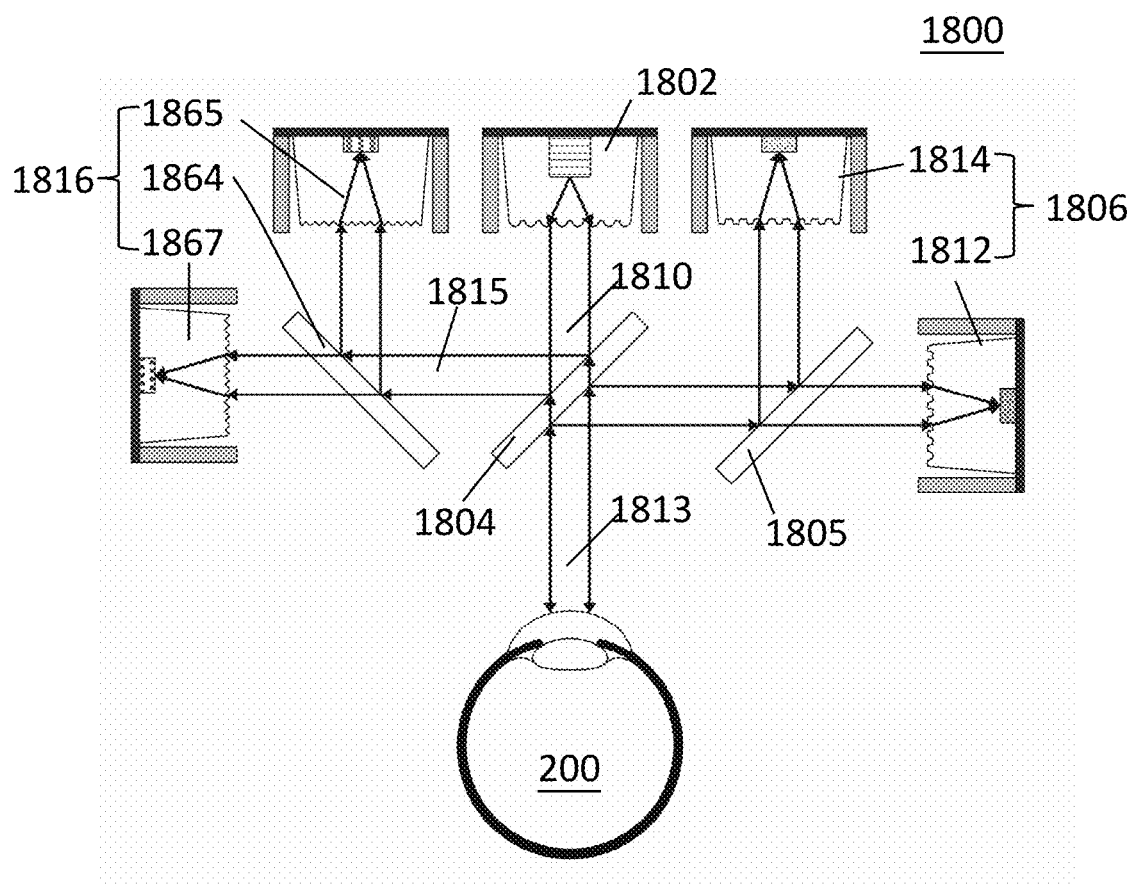
FIG. 20 is a schematic diagram illustrating an apparatus for non-invasive glucose monitoring in accordance with an eighteenth exemplary embodiment.

FIG. 20 illustrates an apparatus for non-invasive glucose monitoring in accordance with an eighteenth exemplary embodiment of the present disclosure. The apparatus 1800 includes a light source module 1802, a first beam splitter 1804, a second beam splitter 1805, a set of light detecting modules 1806, and a light information analysis unit 1816. The set of light detecting modules 1806 includes a first light detecting module 1812 and a second light detecting module 1814. The light information analysis unit 1816 includes a third beam splitter 1864, a third light detecting module 1865, and a fourth light detecting module 1867. The optical path of the apparatus 1800 for glucose monitoring is substantially similar to that of the apparatus 1500 of the fifteenth exemplary embodiment, thus the arrangement of main functional components of the apparatus 1800 are not described further for brevity.

Figure 21A:
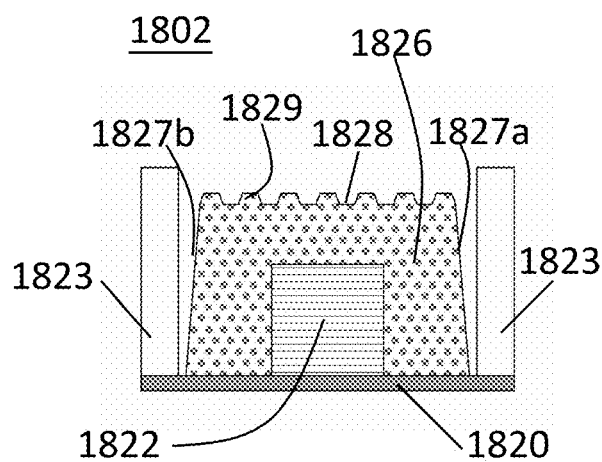
FIG. 21A and FIG. 21B respectively show schematic diagrams of a top view and an oblique sectional view of the light source module of the apparatus of FIG. 20 in accordance with the eighteenth exemplary embodiment.
Figure 21B:
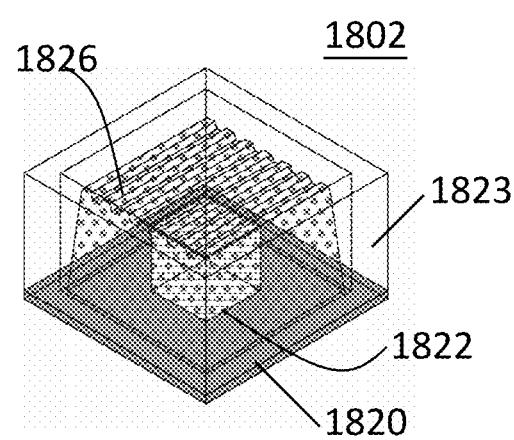

FIG. 21A and FIG. 21B provide a top view and an oblique sectional view, respectively, of the light source module 1802 applied in the apparatus 1800 of the eighteenth embodiment. The light source module 1802 includes a substrate 1820, at least one light emitting element 1822 mounted on the substrate 1820, an encapsulant 1826 formed over the light emitting element 1822, and a peripheral side wall 1823 mounted on the substrate 1820 and surrounding the encapsulant 1826. Particularly, a microstructure 1829 is provided to a top surface of the encapsulant 1826. Features of the substrate 1820, the light emitting element 1822, and the peripheral side wall 1823 are similar to those mentioned relating to the light source module 1602 of the sixteenth embodiment.

Referring to FIG. 21A, in the present embodiment, the encapsulant 1826 has a substantially trapezoid shape, and the encapsulant 1826 has a top surface 1828, a first lateral surface 1827a, and a second lateral surface 1827b. The top surface 1828 is substantially parallel to the substance 1820. A first inclined angle is formed by the first lateral surface 1827a and the substance 1820 and the first inclined angle faces toward the light emitting element 1822. A second inclined angle is formed by the second lateral surface 1827b and the substance 1820 and the second inclined angle faces toward the light emitting element 1822. Both the first and the second inclined angles are smaller than 90 degrees in the present embodiment. Although the first inclined angle and the second inclined angle are shown to be almost equal in the present exemplary embodiment, it should be noted that the first inclined angle may be different from the second inclined angle in other embodiments. The encapsulant 1826 may be constructed as one single layer or as multiple layers with gradually decreasing refractive indices, as mentioned hereinabove. Other details of the encapsulant 1826 are similar to those mentioned related to the encapsulant 1626 in the sixteenth embodiment.

In the present exemplary embodiment, a microstructure 1829 is provided to the top surface 1828 of the encapsulant 1826 to increase the light extraction efficiency of the light source module 1802 of the apparatus 1800. The microstructure 1829 may be a refractive microstructure or a diffractive microstructure, which is able to concentrate the light emitted by the light emitting element 1822 toward the first beam splitter 1804 after the light passes through the microstructure 1829. The refractive microstructure may be a Fresnel lens microstructure; the diffractive microstructure may be a diffractive optical element (DOE) microstructure. The microstructure 1829 may be formed as a set of microgrooves on the surface of an encapsulant by injection molding or compression molding. The microstructure 1829 may be embodied as a set of concentric circles or a set of concentric arcs. It should be noted that in other embodiments, the microstructure may be combined with an optical directional component, that is, a geometric optical component having a refractive index which is distinct from adjacent substances, to concentrate the emitted light toward the first beam splitter 1804. The optical directional component may be an encapsulant having an inclined plane or a curvature surface, arranged on the top surface of the encapsulant.

Figure 21C:
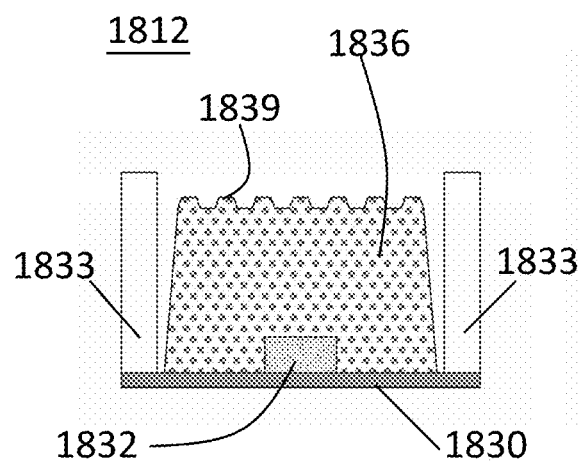
FIG. 21C and FIG. 21D respectively show schematic diagrams of a top view and an oblique sectional view of the first light detecting module of the apparatus of FIG. 20 in accordance with the eighteenth exemplary embodiment.
Figure 21D:
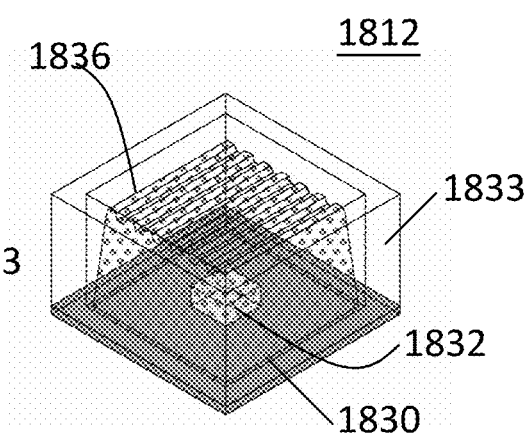

To improve the light receiving efficiency, each of the light detecting modules (1812, 1814, 1865, and 1867) may also be constructed as a packaged optical module, which includes an encapsulant sealing a photo detector. Taking the first light detecting module 1812 as an example, FIG. 21C and FIG. 21D provide a top view and an oblique sectional view, respectively, of the first light detecting module 1812 applied in the apparatus 1800 of the eighteenth embodiment. The first light detecting module 1812 includes a substrate 1830, at least one photo detector 1832 mounted on the substrate 1830, an encapsulant 1836 formed over the photo detector 1832, and a peripheral side wall 1833 mounted on the substrate 1830 surrounding the encapsulant 1836. Particularly, a microstructure 1839 is provided to a top surface of the encapsulant 1836. Details of the substrate 1830, the photo detector 1832, the peripheral side wall 1833 are similar to those mentioned relating to the first light detecting module 1612 of the sixteenth embodiment, and details of the encapsulant 1836 and the microstructure 1839 are similar to those mentioned relating to the encapsulant 1826 and the microstructure 1829 of the present embodiment.

Referring to FIG. 20, although the encapsulant 1826 of the light source module 1802 and four encapsulants of the light detecting modules (1812, 1814, 1865, 1867) in the apparatus 1800 are presented by same patterns, it should be noted that the encapsulant 1826 of the light source module 1802 has a different function as regards the optical path of the apparatus 1800, compared to the function of encapsulants (such as the encapsulant 1836) of the light detecting modules. Thus, the optical characteristic (for example, the shape and the refractive index) of the encapsulant 1826 is different from that of the other four encapsulants of the light detecting modules. Moreover, each of the encapsulants of the light detecting modules (1812, 1814, 1865, 1867) may also be specifically designed and different from each other. Similarly, microstructures provided to each encapsulant may also be different from each other.

Figure 22A:
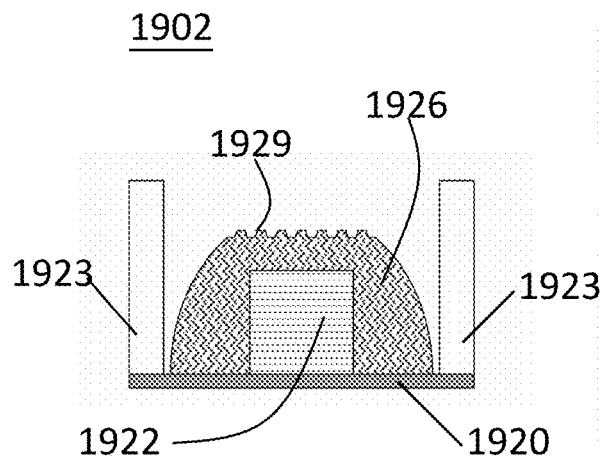
FIG. 22A and FIG. 22B respectively show schematic diagrams of a top view and an oblique sectional view of a light source module in accordance with a nineteenth exemplary embodiment.
Figure 22B:
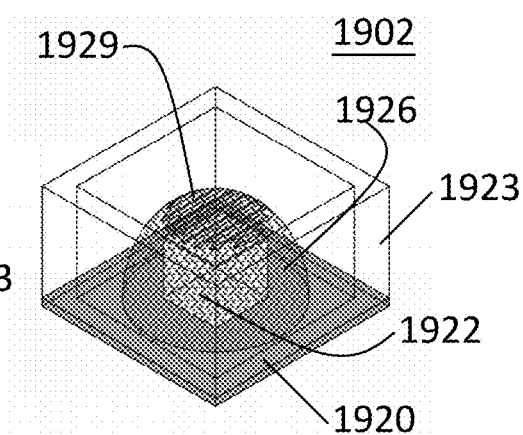
Figure 22C:
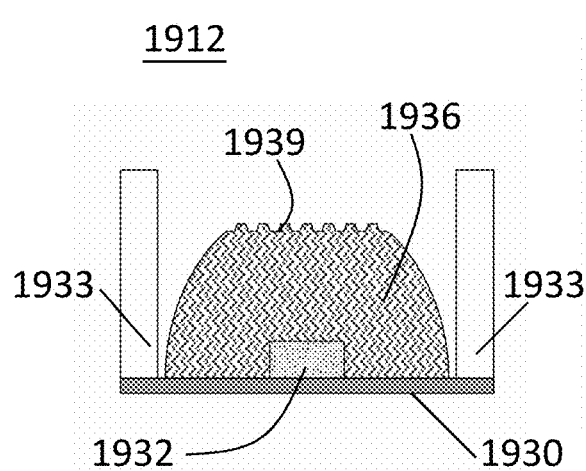
FIG. 22C and FIG. 22D respectively show schematic diagrams of a top view and an oblique sectional view of a light detecting module in accordance with the nineteenth exemplary embodiment.
Figure 22D:
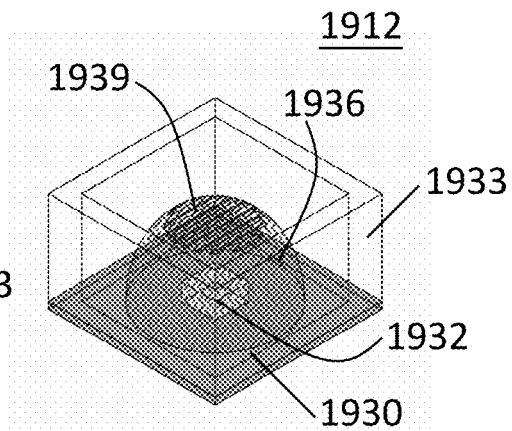

FIG. 22A-22D provide an alternative embodiment of the packaged optical modules having spherical segment shape encapsulants with microstructures, which may be applied in any apparatus of the exemplary embodiments in the present disclosure. FIG. 22A and FIG. 22B provide a top view and an oblique sectional view, respectively, of a light source module 1902 in accordance with a nineteenth exemplary embodiment. FIG. 22C and FIG. 22D provide a top view and an oblique sectional view, respectively, of a light detecting module 1912 in accordance with the nineteenth exemplary embodiment. The light detecting module 1912 may be applied together with the light source module 1902 or any other light source module mentioned in the present disclosure in one apparatus for glucose monitoring.

The light source module 1902 includes a substrate 1920, at least one light emitting element 1922 mounted on the substrate 1920, an encapsulant 1926 formed over the light emitting element 1922, and a peripheral side wall 1923 mounted on the substrate 1920 and surrounding the encapsulant 1926. The encapsulant 1926 is substantially a spherical segment shape, that is, a sphere cut by a pair of parallel planes. A microstructure 1929 is provided to a top surface of the encapsulant 1926, configured to concentrate light emitted by the light emitting element 1922 toward a predetermined direction (such as toward an optical element in the apparatus). The light emitted by the light emitting element 1922 is directed by the encapsulant 1926 and the microstructure 1929, thereby improving the measurement efficiency.

The light detecting module 1912 includes a substrate 1930, at least one photo detector 1932 mounted on the substrate 1930, an encapsulant 1936 formed over the photo detector 1932, and a peripheral side wall 1933 mounted on the substrate 1930 and surrounding the encapsulant 1936. The encapsulant 1936 is substantially a spherical segment shape and a microstructure 1939 is provided to a top surface of the encapsulant 1936, which is configured to concentrate light toward the photo detector 1932 for detection. Thus, the light receiving efficiency is improved.

It should be noted that the packaged optical modules in one apparatus may have different constructions. For example, in one apparatus for glucose monitoring, a light source module of the apparatus may have a collimating element, one light detecting module may have an encapsulant sealing a photo detector, while another light detecting module may have an encapsulant with a microstructure (or an optical directional component) sealing a photo detector. Moreover, more than one optical element (a collimating element, an encapsulant, an optical directional component, an embedded microstructure, etc.) may be applied in one single packaged optical module to further improve the light utilization efficiency.

Figure 23A:
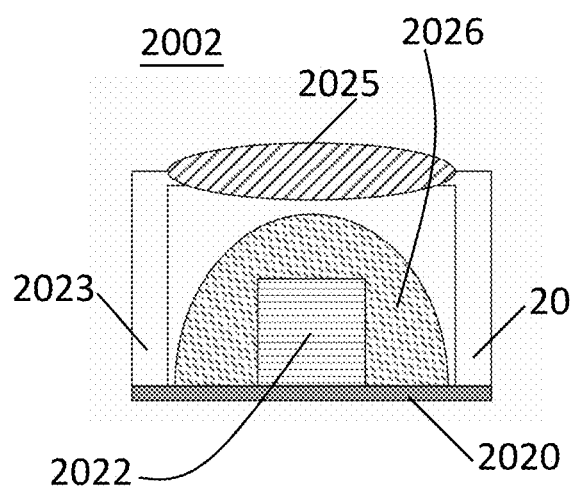
FIG. 23A and FIG. 23B respectively show schematic diagrams of a top view and an oblique sectional view of a light source module in accordance with a twentieth exemplary embodiment.
Figure 23B:
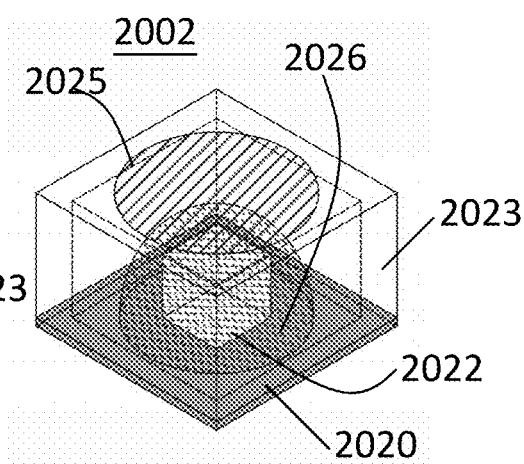
Figure 23C:
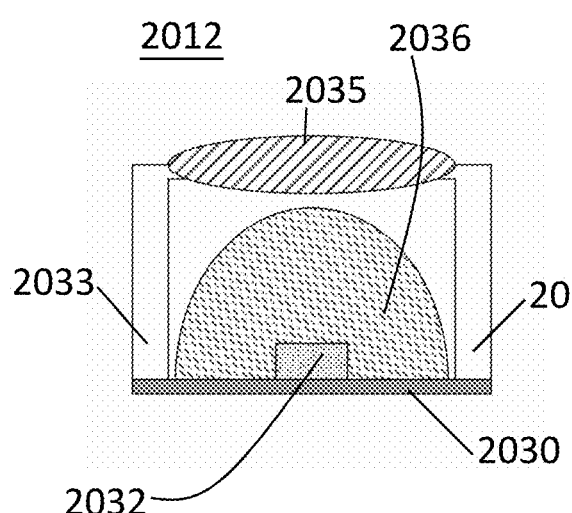
FIG. 23C and FIG. 23D respectively show schematic diagrams of a top view and an oblique sectional view of a light detecting module in accordance with the twentieth exemplary embodiment.
Figure 23D:
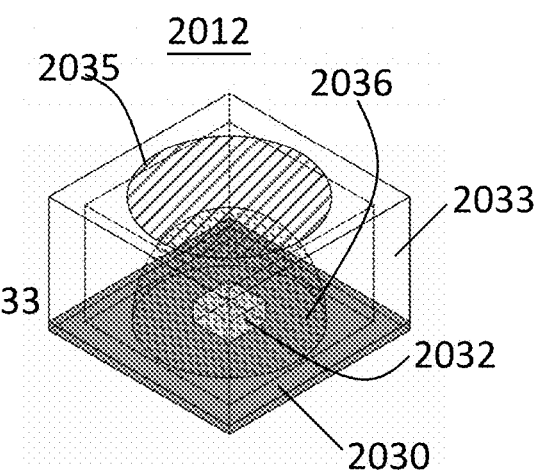

FIG. 23A and FIG. 23B provide a top view and an oblique sectional view, respectively, of a light source module 2002, and FIG. 23C and FIG. 23D provide a top view and an oblique sectional view, respectively, of a light detecting module 2012 in accordance with a twentieth exemplary embodiment. The light source module 2002 and the light detecting module 2012 may be applied in any apparatus of the exemplary embodiments of the present disclosure.

The light source module 2002 includes a substrate 2020, at least one light emitting element 2022 mounted on the substrate 2020, a domed shape encapsulant 2026 formed over the light emitting element 2022, and a peripheral side wall 2023 mounted on the substrate 2020 and surrounding the encapsulant 2026, which are similar to the light source module 1602 shown in FIGS. 18A-18B in accordance with the sixteenth embodiment mentioned hereinabove. Particularly, the light source module 2002 includes a collimating element 2025 for improving the light extraction efficiency. The collimating element 2025 is configured for narrowing the emitted light. The collimating element 2025 may make the direction of the emitted light become more aligned in a specific direction. For example, the collimating element 2025 may provide collimated light or parallel rays or may make the spatial cross section of the emitted light become smaller. In the present embodiment, the collimating element 2025 is a collimating lens positioned at one side of the encapsulant 2026 away from the substrate 2020. Thereby, the light emitted by the light emitting element 2022 is confined by the encapsulant 2026 and the collimating element 2025 before the light is projected to other optical elements (such as a first beam splitter) of the apparatus.

Similarly, the light detecting module 2012 includes a substrate 2030, at least one photo detector 2032 mounted on the substrate 2030, an encapsulant 2036 formed over the photo detector 2032, a peripheral side wall 2033 mounted on the substrate 2030 and surrounding the encapsulant 2036, and a collimating element 2035 for improving the light receiving efficiency. The collimating element 2035 is configured for narrowing the incident light received by the light detecting module 2012. The collimating element 2035 may make the direction of the incident light become more aligned in a specific direction (i.e., providing collimated light or parallel rays). The collimating element 2035 may make the spatial cross section of the incident light become smaller. In the present embodiment, the collimating element 2035 is a collimating lens positioned at one side of the encapsulant 2036 away from the substrate 2030. Thereby, the incident light received by the light detecting module 2012 is confined by the collimating element 2035 and the encapsulant 2036 before the light is measured by the photo detector 2032.

It can be understood that the light detecting module 2012 may be applied to measure light reflected from an eyeball or light from emitted light that does not enter the eyeball. For example, an example of the apparatus for glucose monitoring may include four light detecting modules 2012. Two of such light detecting modules 2012 are applied for measuring light reflected from an eyeball, the other two are applied in a light information analysis system for measuring emitted light that does not enter the eyeball.

Figure 24A:
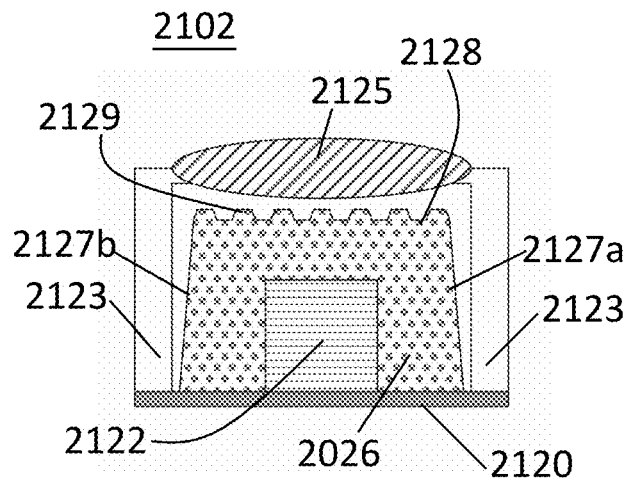
FIG. 24A and FIG. 24B respectively show schematic diagrams of a top view and an oblique sectional view of a light source module in accordance with a twenty-first exemplary embodiment.
Figure 24B:
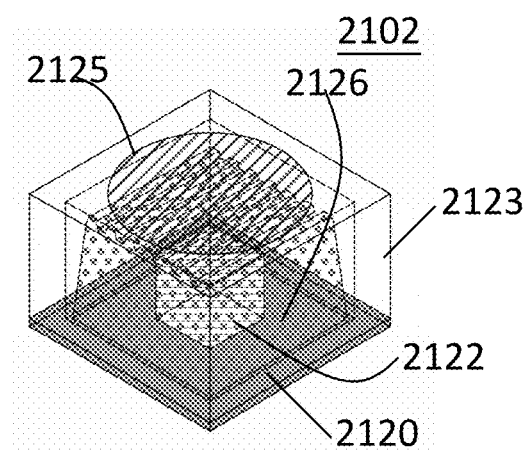
Figure 24C:
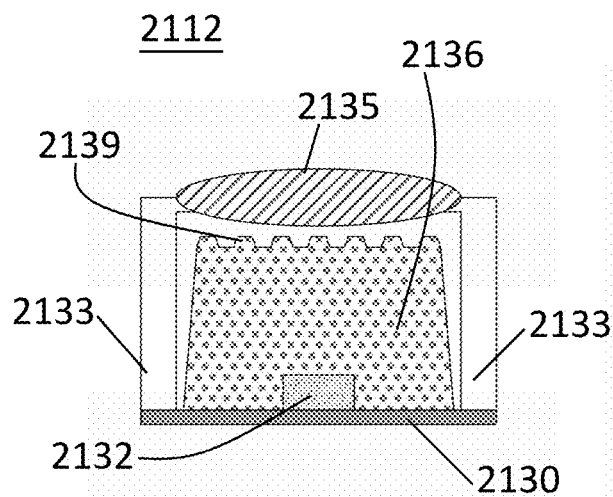
FIG. 24C and FIG. 24D respectively show schematic diagrams of a top view and an oblique sectional view of a light detecting module of the apparatus in accordance with the twenty-first embodiment.
Figure 24D:
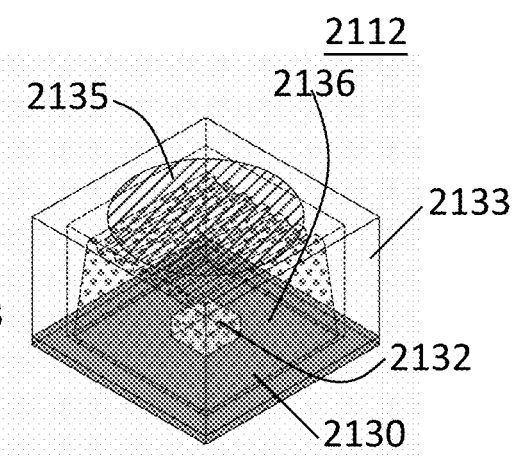

FIG. 24A and FIG. 24B provide a top view and an oblique sectional view, respectively, of a light source module 2102, and FIG. 24C and FIG. 24D provide a top view and an oblique sectional view, respectively, of a light detecting module 2112 in accordance with a twenty-first exemplary embodiment. The light source module 2102 and the light detecting module 2112 may be applied in any apparatus of the exemplary embodiments of the present disclosure.

The light source module 2102 includes a substrate 2120, at least one light emitting element 2122 mounted on the substrate 2120, a trapezoid shape encapsulant 2126 formed over the light emitting element 2122, a peripheral side wall 2123 mounted on the substrate 2120 and surrounding the encapsulant 2126, and a collimating element 2125. Compared to the light source module 2002 in the previous embodiment, a top surface of the encapsulant 2126 is provided with a microstructure 2129.

As shown in FIG. 24A, the encapsulant 2126 has a top surface 2128, a first lateral surface 2127a and a second lateral surface 2127b. The top surface 2128 is substantially parallel to the substance 2120. The encapsulant 2126 is provided with a microstructure 2129 at the top surface 2128. In one alternative embodiment, the microstructure may be replaced by an optical directional component. In another alternative embodiment, the microstructure may be combined with an optical directional component. The collimating element 2125 is configured for further narrowing the emitted light. In the present embodiment, the collimating element 2125 is a collimating lens positioned at one side of the encapsulant 2126 away from the substrate 2120. Thereby, the light emitted by the light emitting element 2122 is confined by the encapsulant 2126, by the microstructure 2129 (and/or an optical directional component), and by the collimating element 2125 before the light is projected to other optical elements (such as a first beam splitter) of the apparatus, thereby improving the light extraction efficiency. Other details of the light source module 2102 are similar to the light source modules mentioned above.

Similarly, the light detecting module 2112 includes a substrate 2130, at least one photo detector 2132 mounted on the substrate 2130, a trapezoid shape encapsulant 2136 formed over the photo detector 2132, a peripheral side wall 2133 mounted on the substrate 2130 and surrounding the encapsulant 2136, and a collimating element 2135. Particularly, a top surface of the encapsulant 2136 is provided with a microstructure 2139.

The encapsulant 2136 is configured to improve the light receiving efficiency of the light detecting module 2112. The microstructure 2139 may be a refractive microstructure or a diffractive microstructure, which is able to concentrate an incident light toward a desired direction, such as the photo detector 2132. The collimating element 2135 is configured for narrowing the incident light received by the light detecting module 2112. In the present embodiment, the collimating element 2135 is a collimating lens positioned at one side of the encapsulant 2136 away from the substrate 2130. Thereby, the incident light received by the light detecting module 2112 is confined by the collimating element 2135, by the microstructure 2139 (or/and an optical directional component) and by the encapsulant 2136 before the light is measured by the photo detector 2132, thereby improving the light receiving efficiency.

It can be understood that the light detecting module 2112 may be applied to measure light reflected from an eyeball or light from emitted light that does not enter the eyeball. For example, an example of the apparatus for glucose monitoring may include four light detecting modules 2112: two light detecting modules 2112 for measuring light reflected from an eyeball; the other two light detecting modules 2112 applied in a light information analysis system for measuring light from emitted light that does not enter the eyeball.

Figure 25:
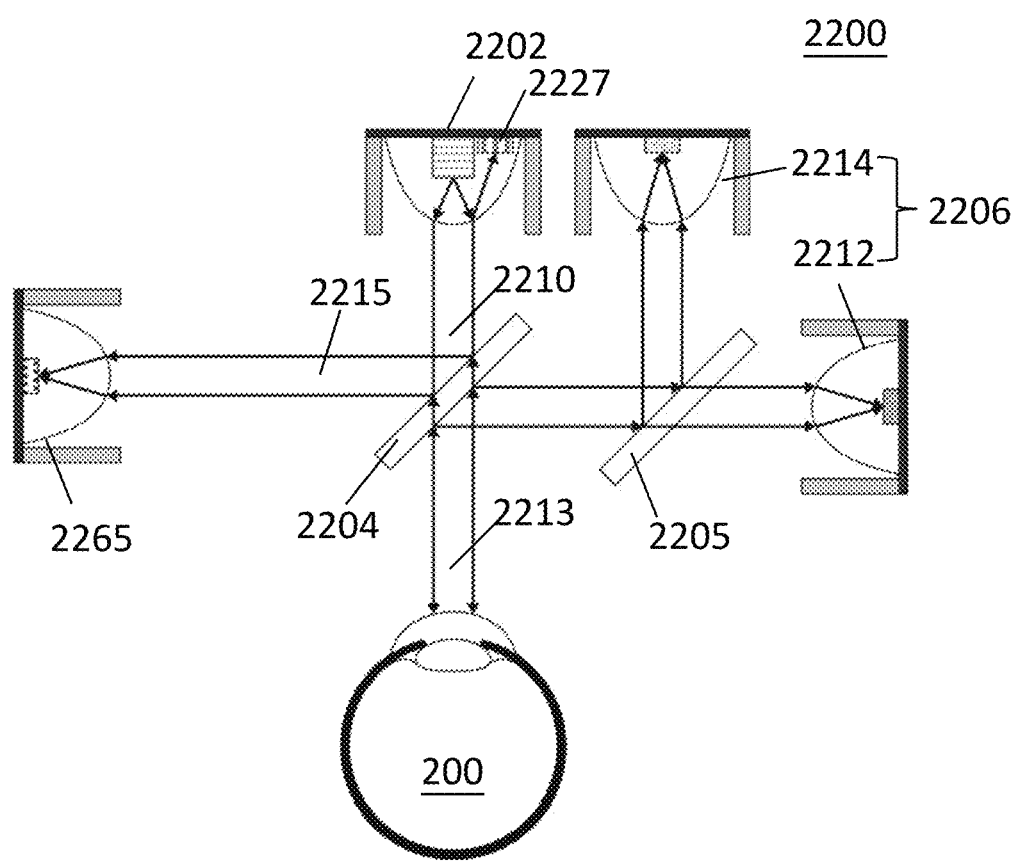
FIG. 25 is a schematic diagram illustrating an apparatus for non-invasive blood glucose monitoring in accordance with a twenty-second exemplary embodiment.

FIG. 25 illustrates an apparatus for non-invasive glucose monitoring in accordance with a twenty-second exemplary embodiment of the present disclosure. The apparatus 2200 includes a light source module 2202, a first beam splitter 2204, a second beam splitter 2205, a set of light detecting modules 2206, and a light information analysis unit (not shown). The set of light detecting modules 2206 includes a first light detecting module 2212 and a second light detecting module 2214. The light information analysis unit (not shown) includes a third light detecting module 2265. Particularly, the light source module 2202 includes an optical power sensor 2227 for feedback control. The power sensor is configured to measure the power of the emitted light. The power of the emitted light may be directly measured by the light power partially directed from the emitted light or may be indirectly measured from the temperature of the light source module 2202. For example, the power sensor may be a photodetector or a thermometer.

Referring to FIG. 25, the light source module 2202 generates a light beam 2210. The light beam 2210 is split into two parts by the first beam splitter 2204. A first light beam 2213 passes through the first beam splitter 2204 and a second light beam 2215 is reflected by the first beam splitter 2204.

The first light beam 2213 enters into an eyeball 200 of an object, whereby generating reflected light from the eyeball 200. The reflected light from the eyeball 200 is reflected by the first beam splitter 2204, and is then split into two parts by the second beam splitter 2205. One part of the light that passes through the second beam splitter 2205 is detected by the first light detecting module 2212, the other part of the light that is reflected by the second beam splitter 2205 is detected by the second light detecting module 2214. The first light detecting module 2212 may be configured to measure optical angular information of received light, while the second light detecting module 2214 may be configured to measure energy information of received light. The second light beam 2215, which may present light information of the light generated by the light source module 2202, is detected by the third light detecting module 2265. The third light detecting module 2265 is configured to measure optical angular information of light. As shown in FIG. 25, each of the light detecting modules (2212, 2214, and 2265) is a packaged optical module having a photodetector, and is sealed by an encapsulant to increase the light receiving efficiency. Details of such light detecting module are described hereinabove.

Figure 26A:
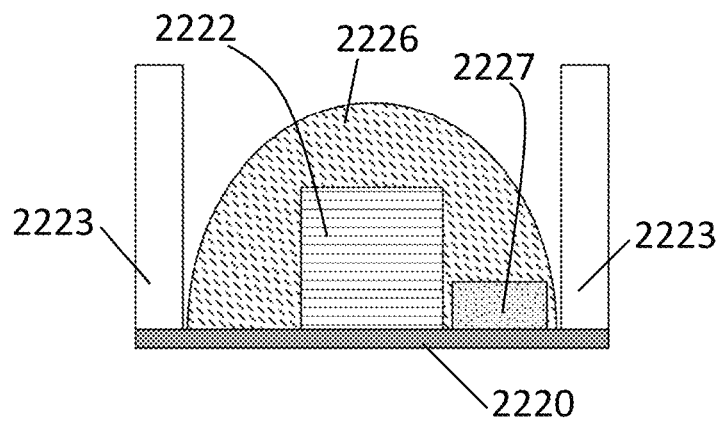
FIG. 26A and FIG. 26B respectively show schematic diagrams of a top view and an oblique sectional view of the light source module of the apparatus of FIG. 25 in accordance with the twenty-second exemplary embodiment.
Figure 26B:
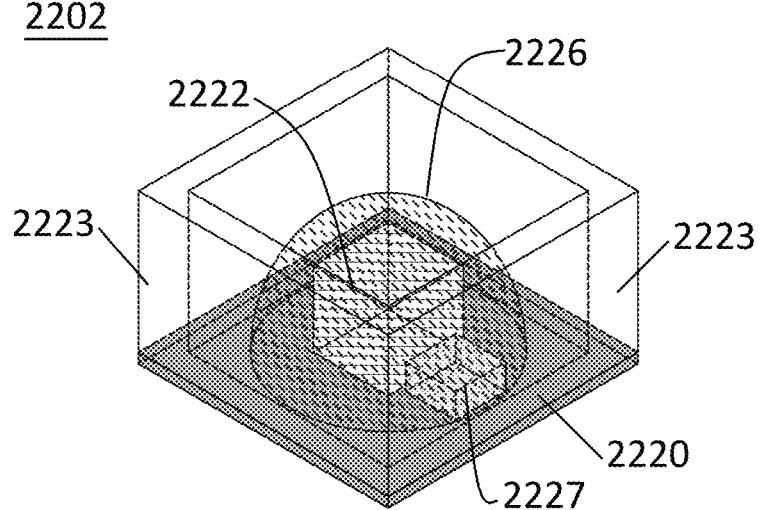

FIG. 26A and FIG. 26B provide a top view and an oblique sectional view, respectively, of the light source module 2202. The light source module 2202 includes a substrate 2220, at least one light emitting element 2222, the optical power sensor 2227 proximate to the light emitting element 2222, an encapsulant 2226 formed over the light emitting element 2222 and the optical power sensor 2227, and a peripheral side wall 2223 mounted on the substrate 2220 and surrounding the encapsulant 2226.

The substrate 2220 may include a printed circuit board (PCB) electrically coupled to the light emitting element 2222 and the optical power sensor 2227. The light emitting element 2222 may be a laser diode. The optical power sensor 2227 is configured to detect the laser output of the light emitting element 2222. The encapsulant 2226 seals the light emitting element 2222 and the optical power sensor 2227. The encapsulant 2226 is configured to improve the light extraction efficiency of the light source module 2202. In the present embodiment, the encapsulant 2226 may reflect a part of the emitted light toward the optical power sensor 2227 for feedback control. The peripheral side wall 2223 is mounted on the substrate 2220, and the encapsulant 2226 is surrounded by the peripheral side wall 2223, providing a packaged optical module.

The optical power sensor 2227, configured to detect the laser output of the light emitting element 2222, may be a thermal power sensor or a photodiode power sensor. Generally, a thermal power sensor, such as a thermopile laser sensor, is capable of converting the radiation from an incident laser into heat energy at a surface of the thermal power sensor. This heat input produces a temperature gradient across the sensor and a voltage is generated by the temperature gradient according to the thermoelectric effect. Since the voltage is directly proportional to the strength of the incident laser, it can be directly related to the irradiation power. A photodiode power sensor converts light into an electrical current. Compared to the thermal power sensor, the photodiode power sensor is more sensitive to the light wavelength and the incident angle of light, thus the selection of the type of the optical power sensor 2227 depends on the design and cost of the apparatus 2200. Moreover, both the optical power sensor 2227 and the light emitting element 2222 may be coupled to a processing unit (not shown) of the apparatus 2200 to control the laser output of the light emitting element 2222.

It can be noted that in the exemplary embodiments shown in FIGS. 15, 17, 19, and 20, two light detecting modules are applied in an information analysis unit of the apparatus for glucose monitoring, to detect the optical angular information and the energy information of the generated light from the light source module. In the present embodiment, as shown in FIG. 25, as the energy information of the emitted light may be obtained by the optical power sensor 2227 of the light source module 2202, only one light detecting module (i.e. the third light detecting module 2265) is applied to obtain light information of the light from the first beam splitter 2204. Therefore, the apparatus 2200 may be more compact to improve the portability of the apparatus.

Figure 27A:
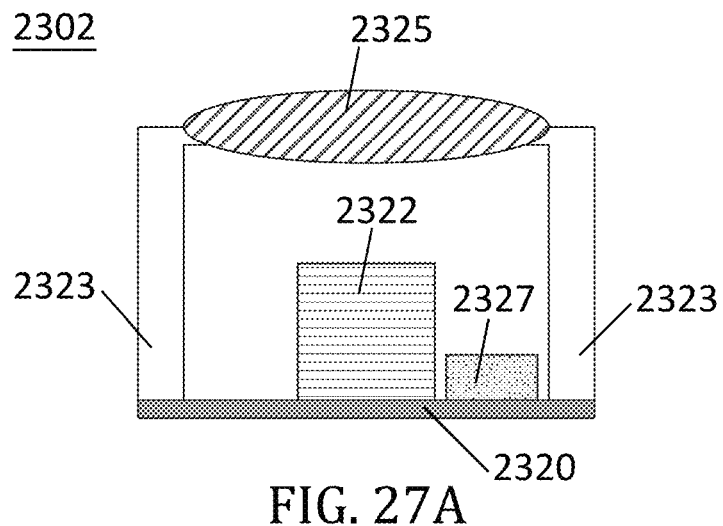
FIG. 27A and FIG. 27B respectively show schematic diagrams of a top view and an oblique sectional view of a light source module in accordance with an alternative exemplary embodiment.
Figure 27B:
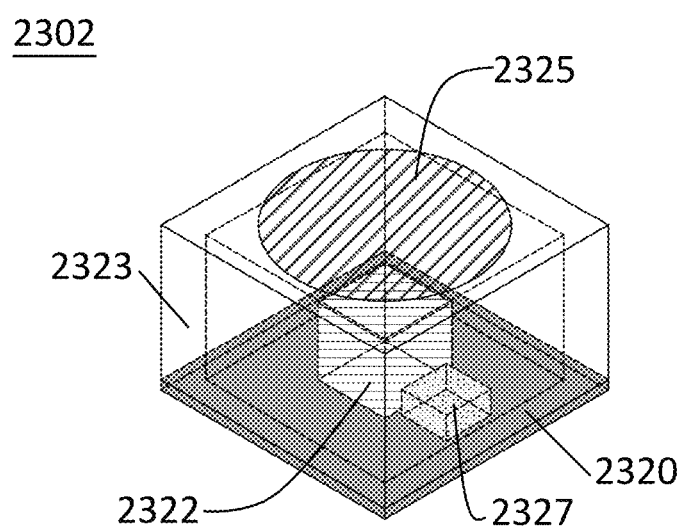
Figure 28A:
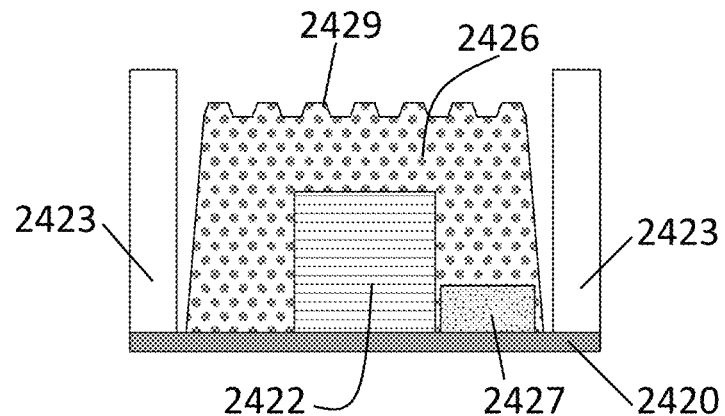
FIG. 28A and FIG. 28B respectively show schematic diagrams of a top view and an oblique sectional view of a light source module of in accordance with another alternative exemplary embodiment.
Figure 28B:
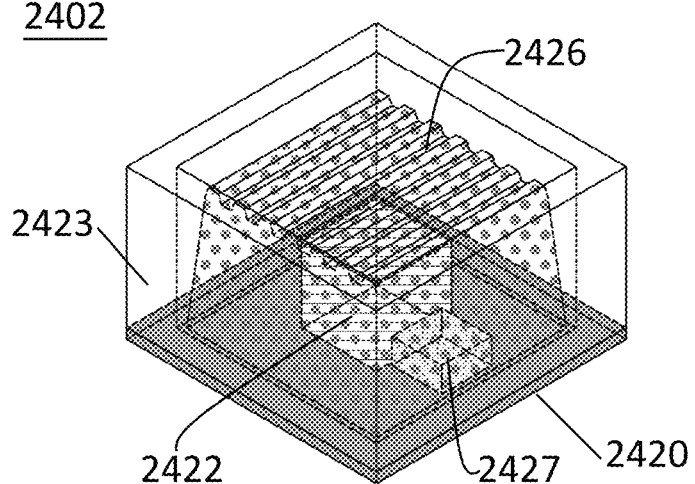

Alternatively, FIGS. 27A-28B provide alternative exemplary embodiments of the light source module, which may be applied in the apparatus 2200. FIG. 27A and FIG. 27B show a top view and an oblique sectional view, respectively, of a light source module 2302. The light source module 2302 includes a substrate 2320, at least one light emitting element 2322, an optical power sensor 2327 proximate to the light emitting element 2322, and a peripheral side wall 2323 mounted on the substrate 2320. A collimating element 2325, instead of an encapsulant, is configured to reflect a part of the emitted light toward the optical power sensor 2327 for feedback control, and to concentrate the emitted light passing through the collimating element 2325 toward a predetermined direction. FIG. 28A and FIG. 28B show a top view and an oblique sectional view, respectively, of a light source module 2402. The light source module 2402 includes a substrate 2420, at least one light emitting element 2422, an optical power sensor 2427 proximate to the light emitting element 2422, and a peripheral side wall 2423 mounted on the substrate 2420. A microstructure 2429 is provided to an encapsulant 2426 to further confine the emitted light passing through the encapsulant 2426 toward a predetermined direction, while the encapsulant 2426 also reflects a part of the emitted light back to the optical power sensor 2427, for feedback control. Details of the light source module 2302 and 2402 are mentioned hereinabove.

In summary, the above embodiments at least include the following features:

(1). The apparatus for non-invasive blood glucose monitoring provided by the aforementioned exemplary embodiments may be used to measure the glucose information accurately (e.g., concentration of glucose) of the measuring object, and since the concentration of glucose in the eyeball (e.g., aqueous humor within the eyeball) has a relationship with the concentration of blood glucose, the blood glucose information (e.g., concentration of blood glucose) may be read according to the relationship.

(2). The portable mobile device with a non-invasive blood glucose monitoring function provided by the aforementioned exemplary embodiments may be miniaturized in applications, so as to improve utilization convenience.

(3). Utilization environments of the portable mobile device with a non-invasive blood glucose monitoring function provided by the aforementioned exemplary embodiments have no special restriction, thus may be used indoors and outdoors.

(4). The concentration of blood glucose of the measuring object may be continuously obtained in real time according to the method for non-invasive blood glucose monitoring provided by the aforementioned exemplary embodiments.

(5). The analysis method for the biological molecule provided by the aforementioned exemplary embodiment may obtain the target molecule concentration which simultaneously exists in the target molecule and the interference molecule, through the optical angular difference values and the absorption energy difference values; therefore, a more accurate assessment of the concentration of target molecule may be obtained.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

The exemplary embodiments shown and described above are only examples. Many details are often found in the art such as the other features of an electronic device for optical detection of blood glucose. Therefore, many such details are neither shown nor described. Even though numerous characteristics and advantages of the present disclosure have been set forth in the foregoing description, together with details of the structure and function of the present disclosure, the disclosure is illustrative only, and changes may be made in the details, especially in matters of shape, size, and arrangement of the parts within the principles of the present disclosure, up to and including the full extent established by the broad general meaning of the terms used in the claims. It will therefore be appreciated that the exemplary embodiments described above may be modified within the scope of the claims.

What is claimed is:

1. A method for non-invasive glucose monitoring by measuring at least two properties of reflected light from inside an eyeball and using a process that uses the two measured properties together to do the glucose monitoring, the method comprising:

emitting, using at least one light source, at least one ray of light, and the at least one light source is packaged in an optical module;

transmitting, using a first beam splitter having a focusing function, the light emitted from the light source into an anterior chamber of the eyeball, and the optical module comprises a collimating element to concentrate the emitted light toward the first beam splitter;

focusing, using the first beam splitter, the light on the anterior chamber of the eyeball, whereby the reflected light from the anterior chamber of the eyeball is generated;

simultaneously measuring, using a set of light sensing elements, the at least two properties of the reflected light from the eyeball transmitted by the first beam splitter and a polarizer to the set of light sensing elements, the measured at least two properties comprising optical angular information of the polarized light and absorption energy information of the reflected light simultaneously obtaining, using a processing unit, an optical angular difference and an absorption energy difference between the light emitted from the light source and the reflected light transmitted to the set of light sensing elements by processing the at least two measured properties; and obtaining, using the processing unit, a biological molecule information of a biological molecule by analyzing both the optical angular difference and the absorption energy difference using at least one first polynomial equation and at least one second polynomial equation, the first polynomial equation representing a relationship between the biological molecule information and the optical angular difference, and the second polynomial equation representing a relationship between the biological molecule information and the absorption energy difference;

wherein the biological molecule at least comprises a glucose, and the biological molecule information comprises the glucose information.

2. The method of claim 1, wherein each of the light sensing elements is packaged in another optical module, the another optical module comprises a collimating element to concentrate light toward the light sensing element.

3. The method of claim 1, wherein each of the light sensing elements is packaged in another optical module, the another optical module comprises an encapsulant formed over the light sensing element.

4. The method of claim 3, wherein the encapsulant comprises a top surface, and an optical directional component is arranged at the top surface.

5. The method of claim 3, wherein the encapsulant comprises a top surface, and an optical microstructure is arranged at the top surface.

6. The method of claim 1, further comprising converging the reflected light toward at least one of the light sensing elements by a converging lens.

7. The method of claim 1, further comprising a power sensor for measuring output power of the at least one light source, wherein the power sensor and the at least one light source are packaged in the optical module.

8. The method of claim 7, wherein the power sensor is a photodetector.

9. The method of claim 7, wherein the power sensor is a thermometer.

10. A method for non-invasive glucose monitoring by measuring at least two optical properties of reflected light from inside an eyeball and using a process that uses the two measured optical properties together to do the glucose monitoring, the method comprising:

emitting, using at least one light source, at least one ray of light, and the at least one light source is packaged in an optical module;

transmitting, using a first beam splitter having a focusing function, the light emitted from the light source into an anterior chamber of the eyeball, and the optical module comprises a collimating element to concentrate the emitted light toward the first beam splitter;

focusing, using the first beam splitter, the light in the anterior chamber of the eyeball, whereby the reflected light is generated from the anterior chamber of the eyeball;

simultaneously measuring, using a set of light sensing elements, the at least two optical properties of the reflected light reflected from the eyeball to the set of light sensing elements;

wherein measuring the at least two optical properties of the reflected light from the eyeball comprises measuring both optical angular information of a polarized light through a polarizer and absorption energy information of the reflected light; and simultaneously determining, using a processing unit, the glucose information of the eyeball using both the optical angular information and the absorption energy information of the reflected light from the eyeball using at least one first polynomial equation and at least one second polynomial equation, the first polynomial equation representing a relationship between the glucose information and the optical angular information, and the second polynomial equation representing a relationship between the glucose information and the absorption energy information.

11. The method of claim 10, wherein each of the light sensing elements is packaged in another optical module, the another optical module comprises a collimating element to concentrate light toward the light sensing element.

12. The method of claim 10, wherein each of the light sensing elements is packaged in another optical module, the another optical module comprises an encapsulant formed over the light sensing element.

13. The method of claim 12, wherein the encapsulant comprises a top surface, and an optical directional component is arranged at the top surface.

14. The method of claim 12, wherein the encapsulant comprises a top surface, and an optical microstructure is arranged at the top surface.

15. The method of claim 10, further comprising converging the reflected light toward at least one of the light sensing elements by a converging lens.

16. The method of claim 10, further comprising a power sensor for measuring output power of the at least one light source, wherein the power sensor and the at least one light source are packaged in the optical module.

17. The method of claim 16, wherein the power sensor is a photodetector.

18. The method of claim 16, wherein the power sensor is a thermometer.

* * * * *